United States Patent
den Boer et al.

(10) Patent No.: US 11,473,102 B2
(45) Date of Patent: Oct. 18, 2022

(54) ***PERONOSPORA* RESISTANCE IN *SPINACIA OLERACEA***

(71) Applicant: Rijk Zwaan Zaadteelt en Zaadhandel B.V., De Lier (NL)

(72) Inventors: Erik den Boer, De Lier (NL); Raoul Jacobus Johannes Maria Frijters, De Lier (NL)

(73) Assignee: RIJK ZWAAN ZAADTEELT EN ZAADHANDEL B.V., De Lier (NL)

( * ) Notice: Subject to any disclaimer, the term of this patent is extended or adjusted under 35 U.S.C. 154(b) by 0 days.

(21) Appl. No.: 17/085,860

(22) Filed: Oct. 30, 2020

(65) Prior Publication Data

US 2022/0135995 A1    May 5, 2022

(51) Int. Cl.
*C12N 15/82* (2006.01)
*C12Q 1/6895* (2018.01)
*C07K 14/415* (2006.01)

(52) U.S. Cl.
CPC ........ *C12N 15/8282* (2013.01); *C07K 14/415* (2013.01); *C12Q 1/6895* (2013.01); *C12Q 2600/13* (2013.01); *C12Q 2600/158* (2013.01)

(58) Field of Classification Search
None
See application file for complete search history.

(56) References Cited

U.S. PATENT DOCUMENTS

| | | |
|---|---|---|
| 9,121,029 B2 | 9/2015 | Van Damme et al. |
| 9,265,275 B2 | 2/2016 | Den Braber |
| 9,402,363 B1 | 8/2016 | Feitsma |
| 9,974,276 B2 | 5/2018 | Feitsma et al. |
| 10,017,781 B2 | 7/2018 | Torjek et al. |
| 10,638,688 B2 | 5/2020 | Feitsma et al. |
| 2005/0183150 A1 | 8/2005 | Torisky et al. |
| 2007/0204368 A1 | 8/2007 | Dale |
| 2009/0300786 A1 | 12/2009 | Baerends |
| 2009/0300788 A1 | 12/2009 | Baerends |
| 2010/0031385 A1 | 2/2010 | Baerends |
| 2012/0054894 A1 | 3/2012 | Den Braber |
| 2013/0055422 A1 | 2/2013 | Baerends |
| 2013/0055454 A1 | 2/2013 | Den Braber |
| 2013/0230635 A1 | 9/2013 | Den Braber |
| 2014/0065287 A1 | 3/2014 | Den Braber |
| 2014/0068799 A1 | 3/2014 | Den Braber |
| 2014/0068801 A1 | 3/2014 | Den Braber et al. |
| 2014/0068804 A1 | 3/2014 | Den Braber |
| 2014/0068805 A1 | 3/2014 | Den Braber |
| 2014/0068806 A1 | 3/2014 | Den Braber |
| 2015/0082483 A1 | 3/2015 | Dijkstra |
| 2015/0101073 A1 | 4/2015 | Brugmans et al. |
| 2015/0240256 A1 | 8/2015 | Brugmans et al. |
| 2016/0152999 A1 | 6/2016 | Torjek et al. |
| 2016/0177330 A1 | 6/2016 | Dijkstra |
| 2017/0027126 A1 | 2/2017 | Dijkstra et al. |
| 2017/0027127 A1 | 2/2017 | Dijkstra et al. |
| 2017/0127641 A1 | 5/2017 | De Visser |
| 2017/0127642 A1 | 5/2017 | De Visser |
| 2017/0327839 A1 | 11/2017 | Feitsma |
| 2018/0042198 A1 | 2/2018 | Feitsma |
| 2019/0127753 A1 | 5/2019 | Kock |
| 2019/0233841 A1 | 8/2019 | Kock et al. |
| 2019/0241905 A1* | 8/2019 | Kock ............. C12N 15/8282 |
| 2020/0017875 A1 | 1/2020 | Kock et al. |

FOREIGN PATENT DOCUMENTS

| | | |
|---|---|---|
| DE | 10 2013 010026 | 12/2014 |
| EP | 2 848 114 A1 | 3/2015 |
| EP | 2 912 940 A1 | 9/2015 |
| WO | 2007/051483 A1 | 5/2007 |
| WO | 2013/064436 A1 | 5/2013 |
| WO | 2015/036378 A1 | 3/2015 |
| WO | 2015/036469 A1 | 3/2015 |
| WO | 2015/171603 A1 | 11/2015 |
| WO | 2018/059653 A1 | 4/2018 |
| WO | 2018/060474 A1 | 4/2018 |

OTHER PUBLICATIONS

2011 APS-IPPC Joint Meeting Abstracts of Presentations, Phytopathology (2011) 101(6) Supplemental, S1, S52.
Adam Bentham, et al., Animal NLRs Provide Structural Insights into Plant NLF Function, Annals of Botany (2017) 119:689-702.
Joydeep Chakraborty, et al., Functional Diversification of Structurally Alike NLR Proteins in Plants, Plant Science (2018) 269:85-93.
J.C. Correll, et al., Spinach: Better Management of Downy Mildew and White Rust Through Genomics, Eur. J. Plant Pathology (Dec. 4, 2010) 129:193-205.
Peter N. Dodds, et al., Six Amino Acid Changes Confined to the Leucine-Rich Repeat β-Strand/β-Turn Motif Determine the Difference between the P and P2 Rust Resistance Specificities in Flax, The Plant Cell (Jan. 2001) vol. 13, p. 163-178.
Timothy K. Eitas, et al., NB-LRR Proteins: Pairs, Pieces, Perception, Partners, and Pathways, Current Opinion in Plant Biology (2010) 13:472-477.

(Continued)

*Primary Examiner* — Bratislav Stankovic
(74) *Attorney, Agent, or Firm* — Duane Morris LLP; Thomas J. Kowalski; Deborah L. Lu

(57) ABSTRACT

The present invention relates to an allele designated alpha-WOLF 27 which confers resistance to at least one *Peronospora farinosa* f. sp. *spinacea* race, wherein the protein encoded by said allele is a CC-NBS-LRR protein that may comprise in its amino acid sequence: a) the motif "MAEIGYSVC" SEQ ID NO: 1 at its N-terminus; and b) the motif "KWMCLR" SEQ ID NO: 2; and wherein the LRR domain of the protein has in order of increased preference at least 95%, 95.5%, 96%, 96.5%, 97%, 97.5%, 98%, 98.5%, 99%, 99.5%, 100% sequence similarity to SEQ ID NO: 10. The allele when present in a spinach plant confers complete resistance to at least *Peronospora farinosa* f. sp. *spinacea* race Pfs:7, Pfs:8, Pfs:9, Pfs:11, Pfs:12, Pfs:13, Pfs:14, Pfs:15, Pfs:17.

24 Claims, No Drawings
Specification includes a Sequence Listing.

(56) References Cited

OTHER PUBLICATIONS

Feng, et al., Identification of New Races and Deviating Strains of the Spinach Downy Mildew Pathogen *Peronospora farinosa* f. sp. *spinaciae*. Plant Disease (Jan. 2014) 98(1):145-152.

Feng Chunda, et al., Construction of a Spinach Bacterial Artificial Chromosome (BAC) Library as a Resource for Gene Identification and Marker Development, Plant Mol Biol Rep (2015) 33:1996-2005.

GenBank Accession No. XP_021842255 (Aug. 1, 2017).

Haiwei H. Guo, et al., Protein Tolerance to Random Amino Acid Change, PNAS (Jun. 22, 2004) vol. 101, No. 25, p. 9205-9210.

Charlotte Hallavant, et al., The First Archaeobotanical Evidence of *Spinacia oleracea* L. (Spinach) in Late 12th—mid 13th Century A.D. France, French National Centre for Scientific Research, Article: Vegetation History and Archaeobotany, Published online May 21, 2013.

B. M. Irish, et al., Three New Races of the Spinach Downy Mildew Pathogen Identified by a Modified Set of Spinach Differentials, Plant Disease (Nov. 2007) vol. 91, No. 11, p. 1392-1396.

B. M. Irish, et al., Characterization of a Resistance Locus (Pfs-1) to the Spinach Downy Mildew Pathogen (*Peronospora farinosa* f. sp. *spinaciae*) and Development of a Molecular Marker Linked to Pfs-1, Pathology, American Phytopathological Society, US (2008) vol. 98, No. 8, p. 894-900.

Merriam Webster Definition of "as" Sep. 27, 2016.

Simona Proietti, et al., Increase of Ascorbic Acid Content and Nutritional Quality in Spinach Leaves During Physiological Acclimation to Low Temperature, Plant Physiology and Biochemistry (2009) vol. 47, p. 717-723.

Dong Qi, et al., Recent Advances in Plant NLR Structure, Function, Localization, and Signaling, Frontiers in Immunology (2013) vol. 4, Article 348, p. 1-10.

Hongbing She, et al., Fine Mapping and Candidate Gene Screening of the Downy Mildew Resistance Gene RPF1 in Spinach, Theoretical and Applied Genetics (2018) 131:2529-2541.

Octavina C.A. Sukarta, et al., Structure-Informed Insights for NLR Functioning in Plant Immunity, Seminars in Cell & Developmental Biology (2016) 56: 134-149.

Yanming Yang, et al., Transgenic Spinach Plants Expressing the Coat Protein of Cucumber Mosaic Virus, In Vitro Cell Dev. Biol.-Plant (1997) 33:200-204.

Peter N. Dodds, et al., Direct protein interaction underlies gene-for-gene specificity and coevolution of the flax resistance genes and flax rust avirulence genes , PNAS (Jun. 6, 2006) vol. 103, No. 23, p. 8888-8893.

Xiaoping Gou, et al., Genome-wide cloning and sequence analysts of leucine-rich repeat receptor-like protein kinase genes in *Arabidopsis thaliana*, BMC Genomics (2010) vol. 11, No. 19, p. 1-15.

Leah McHale, et al., Plant NBSMLRR proteins: adaptable guards, Genome Biology (2006) vol. 7, Issue 4, Article 212, p. 212-212.11.

Moffett et al., Interaction Between Domain of a Plant NBS-LRR Protein in Disease Resistance-Related Cell Death, The EMBO Journal (2002) vol. 21, No. 17, p. 4511-4519.

\* cited by examiner

PERONOSPORA RESISTANCE IN SPINACIA OLERACEA

INCORPORATION BY REFERENCE

All documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

SEQUENCE STATEMENT

The instant application contains a Sequence Listing, which has been submitted electronically and is hereby incorporated by reference in its entirety. Said ASCII copy, is named Y7954-00471SL.txt and is 38.5 kb in size.

FIELD OF THE INVENTION

The invention relates to a gene capable of conferring resistance to a spinach plant against one or more *Peronospora farinosa* f. sp. *spinaciae* races. The invention also relates to a spinach plant, to propagation material of said spinach plant, to a cell of said spinach plant, and to seed of said spinach plant carrying the gene. The invention further relates to a method of producing a spinach plant carrying the gene and to the use of the gene in breeding to confer resistance against *Peronospora farinosa* f. sp. *spinaciae*.

BACKGROUND OF THE INVENTION

Downy mildew (*Peronospora farinosa* f. sp. *spinaciae*) is a major threat for spinach growers because it directly affects the harvested leaves. In spinach, downy mildew is caused by the oomycete *Peronospora farinosa* f. sp. *spinaciae* (formerly known as *P. effusa*). Infection makes the leaves unsuitable for sale and consumption, as it manifests itself phenotypically as yellow lesions on the older leaves, and on the abaxial leaf surface a greyish fungal growth can be observed. The infection can spread very rapidly, and it can occur both in glasshouse cultivation and in soil cultivation. The optimal temperature for formation and germination of *P. farinosa* f sp. *spinaciae* spores is 9 to 12° C., and it is facilitated by a high relative humidity. When spores are deposited on a humid leaf surface they can readily germinate and infect the leaf. Fungal growth is optimal between 8 and 20° C. and a relative humidity of ≥80%, and within 6 and 13 days after infection mycelium growth can be observed. Oospores of *P. farinosa* can survive in the soil for up to 3 years, or as mycelium in seeds or living plants.

To date 17 pathogenic races of spinach downy mildew (Pfs) have been officially identified and characterized, and many new candidates are observed in the field. The 17 officially recognized races of *Peronospora farinosa* f sp. *spinaciae*, are designated Pfs:1 to Pfs:17 (Irish et al. Phtypathol. Vol. 98 pg. 894-900, 2008; Plantum NL (Dutch association for breeding, tissue culture, production and trade of seed and young plants) press release, "Benoeming van Pfs: 14, een nieuwe fysio van valse meeldauw in spinazie", Sep. 19, 2012; Report Jim Correl (Univ. Arkansas) and Steven Koike (UC Cooperative Extension, Monterey County), "Race Pfs: 14—Another new race of the spinach downy mildew pathogen", Sep. 18, 2012; Plantum NL press release, "Denomination of Pfs: 15, a new race of downy mildew in spinach", Sep. 2, 2014; Plantum NL press release, "Denomination of Pfs: 16, a new race of downy mildew in spinach, Mar. 15, 2016; Plantum NL press release, Denomination of Pfs: 17, a new race of downy mildew in spinach", Apr. 16, 2018). Races 4 to 16 were identified between 1990 and 2014, while only recently two new *Peronospora* isolates have been identified, termed UA201519B and US1602, which subsequently have been officially named Pfs:16 and Pfs:17 by the International Working Group on *Peronospora* (IWGP) (Plantum NL (Dutch association for breeding, tissue culture, production and trade of seed and young plants) press release, "Denomination of Pfs: 16, a new race of downy mildew in spinach", Mar. 15, 2016; Plantum NL press release, Denomination of Pfs: 17, a new race of downy mildew in spinach", Apr. 16, 2018. All 17 officially recognized Pfs races are publicly available from the Department of Plant Pathology, University of Arkansas, Fayetteville, Ark. 72701, USA, and also from NAK Tuinbouw, Sotaweg 22, 2371 GD Roelofarendsveen, the Netherlands.

Especially the latest identified *Peronospora* races can break the resistance of many spinach varieties that are currently used commercially worldwide, and they thus pose a serious threat to the productivity of the spinach industry. Therefore, it is crucial to stay at the forefront of developments in this field, as *Peronospora* continuously develops the ability to break the resistances that are present in commercial spinach varieties. For this reason new resistance genes against downy mildew are very valuable assets, and they form an important research focus in breeding and particular in spinach and lettuce breeding. One of the main goals of spinach breeders is to rapidly develop spinach varieties with a resistance to as many *Peronospora* races as possible, including the latest identified races, before these races become wide-spread and pose a threat to the industry.

In commercial spinach varieties resistance against downy mildew is usually caused by so-called R-genes. R-gene mediated resistance is based on the ability of a plant to recognize the invading pathogen. In many cases this recognition occurs after the pathogen has established the first phases of interaction and transferred a so called pathogenicity (or avirulence) factor into the plant cell. These pathogenicity factors interact with host components in order to establish conditions which are favorable for the pathogen to invade the host and thereby cause disease. When a plant is able to recognize the events triggered by the pathogenicity factors a resistance response can be initiated. In many different plant pathogen interaction systems such as the interaction of spinach with different downy mildew strains, the plant initiates these events only after specific recognition of the invading pathogen.

Co-evolution of plant and pathogen has led to an arms race in which a R-gene mediated resistance is sometimes overcome as a consequence of the capability of the pathogen to interact with and modify alternative host targets or the same targets in a different way, such that the recognition is lost and infection can be established successfully resulting in disease. In order to re-establish resistance in a plant, a new R-gene has to be introduced which is able to recognize the mode of action of an alternative pathogenicity factor.

Despite the fact that the durability of R-genes is relatively low, R-genes are in spinach still the predominant form of defense against downy mildew. This is mainly due to the fact that it is the only form of defense that gives absolute resistance. So far plant breeders have been very successful in generating downy mildew resistant spinach varieties by making use of resistance genes residing in the wild germplasm of the crop species. Even though R-genes are extensively used in spinach breeding, until now not much is known of these R-genes.

Only recently it was discovered that the R-genes officially recognized in spinach are in fact all different alleles of the two tightly linked genes, the alpha- and the beta-WOLF genes. This was also the first time that R-genes, or better R-alleles were for the first time characterized at the molecular level, i.e. their nucleotide and amino acid sequence was determined. Although this provides the breeder with tools that increase the efficiency of detecting and selecting R-alleles, adequately responding to newly emerging downy mildew races is still crucial for developing commercially successful spinach varieties.

Citation or identification of any document in this application is not an admission that such document is available as prior art to the present invention.

SUMMARY OF THE INVENTION

Therefore, it is the object of the invention to provide a new resistance allele conferring resistance to a newly emerged downy mildew isolate and to provide molecular biological tools for identifying this new resistance allele.

In the research leading to the present invention, a new allelic variant of the Alpha-WOLF gene as described in WO2018059651 was found. The alpha-WOLF gene encodes a protein that belongs to the CC-NBS-LRR family (Coiled Coil—Nucleotide Binding Site—Leucine-Rich Repeat). Depending on the allelic variant (or the allelic variants) that is (are) present in a spinach plant, said plant will produce a variant of the WOLF protein that confers a certain resistance profile to pathogenic races of *Peronospora farinosa* f. sp. *spinaciae*.

In the context of this invention the term "allele" or "allelic variant" is used to designate a version of the gene that is linked to a specific phenotype, i.e. resistance profile. It was found that a spinach plant may carry one or two WOLF genes. Each of these two WOLF genes encompasses multiple alleles, each allele conferring a particular resistance profile. In the context of this invention an allele or allelic variant is a nucleic acid.

The beta WOLF gene is located on scaffold12735 (sequence: GenBank: KQ143339.1), at position 213573-221884. In case the spinach plant also carries or only carries the alpha-WOLF gene, the alpha-WOLF gene is located at approximately the same location as where the beta-WOLF gene is located on scaffold12735 in the Viroflay genome assembly.

The newly found alpha-WOLF allele provides resistance to at least downy mildew race Pfs:14, Pfs: 15 and Pfs: 17.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved. Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

DEPOSIT INFORMATION

Seeds of a plant that comprise the alpha-WOLF 27 allele of the invention in its genome were deposited with NCIMB Ltd, Ferguson Building, Craibstone Estate, Bucksburn, Aberdeen AB21 9YA, UK, on 9 Oct. 2020, under accession number NCIMB 43668. The deposit was made and accepted pursuant to the terms of the Budapest Treaty. Upon issuance of a patent, all restrictions upon the deposit will be removed, and the deposit is intended to meet the requirements of 37 CFR §§ 1.801-1.809. The deposit will be irrevocably and without restriction or condition released to the public upon the issuance of a patent and for the enforceable life of the patent. The deposit will be maintained in the depository for a period of 30 years, or 5 years after the last request, or for the effective life of the patent, whichever is longer, and will be replaced if necessary during that period.

DETAILED DESCRIPTION OF THE INVENTION

A genome assembly for spinach variety Viroflay—which is susceptible to all known pathogenic races of *Peronospora farinosa* f. sp. *spinaciae*—is publicly available (*Spinacia oleracea* cultivar SynViroflay, whole genome shotgun sequencing project; Bioproject: PRJNA41497; GenBank: AYZV00000000.2; BioSample: SAMN02182572, see also Dohm et al, 2014, *Nature* 505: 546-549). In this genome assembly for Viroflay, the beta-WOLF gene is located on scaffold12735 (sequence: GenBank: KQ143339.1), at position 213573-221884. The sequence covered by this interval may comprise the entire genomic sequence of the beta-WOLF gene of Viroflay, plus 2000 basepairs sequence upstream from the gene, plus the sequence downstream from the gene, up to the locus of the neighbouring gene that is situated downstream from the WOLF gene. Spinach variety Viroflay only possesses a single WOLF gene, namely a beta-WOLF gene, but most other spinach lines harbor a single alpha-type WOLF gene at the same location in the genome. Other spinach lines harbor two WOLF genes at approximately the same location in the genome. In such cases, the two WOLF genes are positioned adjacent to each other. In most spinach lines that harbor two WOLF genes, one of said WOLF genes belongs to the alpha-type, and the other WOLF gene belongs to the beta-type. It was observed that this allelic variation in the WOLF locus is responsible for differences in resistance to pathogenic races of *Peronospora farinosa* f. sp. *spinaciae*.

The difference between an allele of an alpha-WOLF gene and an allele of a beta-WOLF gene lies in the presence of specific conserved amino acid motifs in the encoded protein sequence. As mentioned above, all WOLF proteins possess—from N- to C-terminus—the following domains that are generally known in the art: a coiled coil domain (RX-CC-like, cd14798), an NBS domain (also referred to as "NB-ARC domain", pfam00931; van der Biezen & Jones, 1998, *Curr. Biol.* 8: R226-R228), and leucine-rich repeats (IPR032675) which encompass the LRR domain. In addition, all WOLF proteins comprise in their amino acid sequence the motif "MAEIGYSVC" (SEQ ID NO: 1) at the N-terminus. In addition to this, all alpha-WOLF proteins comprise the motif "KWMCLR" (SEQ ID NO: 2) in their amino acid sequence, whereas all beta-WOLF proteins comprise the motif "HVGCVVDR" (SEQ ID NO: 3) in their amino acid sequence.

The present invention relates to a new *Peronospora farinosa* f. sp. *spinaciae* resistance conferring allele of the alpha-WOLF gene designated alpha-WOLF 27.

In particular, the invention relates to a *Peronospora farinosa* f. sp. *spinaciae* resistance conferring allele designated alpha-WOLF 27 wherein the protein encoded by said allele is a CC-NBS-LRR protein that may comprise in its amino acid sequence: a) the motif "MAEIGYSVC" (SEQ ID NO: 1) at its N-terminus; and b) the motif "KWMCLR" (SEQ ID NO: 2); and wherein the LRR domain of the protein has in order of increased preference at least 95%, 95.3%, 95.5%, 95.8%, 96%, 96.3%, 96.5%, 96.8%, 97%, 97.3%, 97.5%, 97.8%, 98%, 98.3%, 98.5%, 98.8%, 99%, 99.3%, 99.5%, 99.8%, 100% sequence identity to SEQ ID NO: 10. Optionally, the alpha-WOLF 27 allele further may comprise an additional motif in its amino acid sequence, namely "DQEDEGEDN" (SEQ ID NO: 14).

The invention further relates to a *Peronospora farinosa* f. sp. *spinaciae* resistance conferring allele designated alpha-WOLF 27 wherein the protein encoded by said allele is a CC-NBS-LRR protein that may comprise in its amino acid sequence: a) the motif "MAEIGYSVC" (SEQ ID NO: 1) at its N-terminus; and b) the motif "KWMCLR" (SEQ ID NO: 2); and wherein the LRR domain of the protein has in order of increased preference at least 96%, 96.3%, 96.5%, 96.8%, 97%, 97.3%, 97.5%, 97.8%, 98%, 98.3%, 98.5%, 98.8%, 99%, 99.3%, 99.5%, 99.8%, 100% sequence similarity to SEQ ID NO: 10. Optionally, the alpha-WOLF 27 allele further may comprise an additional motif in its amino acid sequence, namely "DQEDEGEDN" (SEQ ID NO: 14).

The invention also relates to an alpha-WOLF 27 allele having an LRR domain which has a sequence that in order in order of increased preference has at least 95%, 95.3%, 95.5%, 95.8%, 96%, 96.3%, 96.5%, 96.8%, 97%, 97.3%, 97.5%, 97.8%, 98%, 98.3%, 98.5%, 98.8%, 99%, 99.1%, 99.2%, 99.3%, 99.4%, 99.5%, 99.6%, 99.7%, 99.8%, 99.9%, 100% sequence identity to SEQ ID NO: 9.

For the purpose of this invention, the LRR domain of the protein of the alpha-WOLF 27 allele is defined as the amino acid sequence that in order of increased preference has at least 95%, 95.3%, 95.5%, 95.8%, 96%, 96.3%, 96.5%, 96.8%, 97%, 97.3%, 97.5%, 97.8%, 98%, 98.3%, 98.5%, 98.8%, 99%, 99.1%, 99.2%, 99.3%, 99.4%, 99.5%, 99.6%, 99.7%, 99.8%, 99.9%, 100% sequence identity to SEQ ID NO: 10.

For the purpose of this invention, the LRR domain of the protein of the alpha-WOLF 27 allele is defined as the amino acid sequence that in order of increased preference has at least 96%, 96.3%, 96.5%, 96.8%, 97%, 97.3%, 97.5%, 97.8%, 98%, 98.3%, 98.5%, 98.8%, 99%, 99.1%, 99.2%, 99.3%, 99.4%, 99.5%, 99.6%, 99.7%, 99.8%, 99.9%, 100% sequence similarity to SEQ ID NO: 10.

The skilled person is familiar with methods for the calculation of sequence similarity and sequence identity. Sequence similarity for an amino acid sequence is calculated using EMBOSS stretcher 6.6.0 (ebi.ac.uk/Tools/psa/emboss_stretcher), using the EBLOSUM62 matrix with settings Gap open penalty: 12 and Gap extend penalty: 2. In case of DNA, sequence similarity is calculated using the DNA full matrix with settings Gap open penalty:16 and Gap extend penalty: 4.

The LRR domain of the alpha-WOLF 27 allele as defined herein can be determined by amplifying and sequencing the genomic DNA encoding for the amino acid sequence of LRR domain using specific primers, and subsequently translating the DNA sequence into an amino acid sequence, thereby applying common sense in choosing the correct reading frame. The skilled person is capable of doing this, using freely available online bioinformatics tools such as can be found at expasy.org/translate/.

The genomic sequence of a LRR domain of an alpha-WOLF gene such as alpha-WOLF 27 can be amplified using a primer pair having a forward primer which is a nucleic acid molecule having the sequence of SEQ ID NO: 4 and a reverse primer which is a nucleic acid molecule having the sequence of SEQ ID NO: 5.

The invention also relates to a nucleic acid molecule which confers resistance to at least one *Peronospora farinosa* f. sp. *spinaciae* race, wherein the protein encoded by said nucleic acid molecule is a CC-NBS-LRR protein that may comprise in its amino acid sequence: a) the motif "MAEIGYSVC" at its N-terminus; and b) the motif "KWMCLR"; and wherein the LRR domain of the protein has in order of increased preference at least 95%, 95.3%, 95.5%, 95.8%, 96%, 96.3%, 96.5%, 96.8%, 97%, 97.3%, 97.5%, 97.8%, 98%, 98.3%, 98.5%, 98.8%, 99%, 99.3%, 99.5%, 99.8%, 100% sequence identity to SEQ ID NO: 10. Optionally this nucleic acid molecule is an isolated nucleic acid molecule.

The invention also relates to a nucleic acid molecule which confers resistance to at least one *Peronospora farinosa* f. sp. *spinaciae* race, wherein the protein encoded by said nucleic acid molecule is a CC-NBS-LRR protein that may comprise in its amino acid sequence: a) the motif "MAEIGYSVC" (SEQ ID NO: 1) at its N-terminus; and b) the motif "KWMCLR" (SEQ ID NO: 2); and wherein the LRR domain of the protein has in order of increased preference at least 96%, 96.3%, 96.5%, 96.8%, 97%, 97.3%, 97.5%, 97.8%, 98%, 98.3%, 98.5%, 98.8%, 99%, 99.3%, 99.5%, 99.8%, 100% sequence similarity to SEQ ID NO: 10. Optionally this nucleic acid molecule is an isolated nucleic acid molecule.

PCR conditions for amplifying the LRR domain-encoding region of an alpha-WOLF gene using primers having SEQ ID NO: 4 and SEQ ID NO: 5 are, using Platinum Taq enzyme (Thermo Fisher Scientific): 3 minutes at 95° C. (initial denaturing step); 40 amplification cycles, each cycle consisting of: 30 seconds denaturation at 95° C., 30 seconds annealing at 60° C., and 30 seconds extension at 72° C.; 2 minutes at 72° C. (final extension step).

The LRR domain of a beta-WOLF gene, e.g. the null allele as present in variety Viroflay, can be amplified using a forward primer which is a nucleic acid molecule having the sequence of SEQ ID NO: 6 and a reverse primer which is a nucleic acid molecule having the sequence of SEQ ID NO: 5.

PCR conditions for amplifying the LRR domain-encoding region of a beta-WOLF gene using primers having SEQ ID NO: 5 and SEQ ID NO: 6 are as follows, using Platinum Taq enzyme (Thermo Fisher Scientific): 3 minutes at 95° C. (initial denaturing step); 40 amplification cycles, each cycle consisting of: 30 seconds denaturation at 95° C., 50 seconds annealing at 58° C. and 50 seconds extension at 72° C.; 2 minutes at 72° C. (final extension step).

Therefore, the invention also relates to a primer pair for amplifying the LRR domain of an alpha-WOLF gene, more in particular for amplifying the LRR domain of an alpha-WOLF 27 allele wherein the forward primer is a nucleic acid molecule having the sequence of SEQ ID NO: 4 and the reverse primer which is a nucleic acid molecule having the sequence of SEQ ID NO: 5. The primers disclosed herein have been specifically designed for selectively amplifying part of a WOLF gene, and not of any other CC-NBS-LRR protein-encoding genes.

The invention relates to an alpha-WOLF 27 allele which has a coding sequence that in order of increased preference has at least 95%, 95.5%, 96%, 96.5%, 97%, 97.5%, 97.8%, 98%, 98.3%, 98.5%, 98.8%, 99%, 99.1%, 99.2%, 99.3%, 99.4%, 99.5%, 99.6%, 99.7%, 99.8%, 99.9%, 100% sequence identity to SEQ ID NO: 12.

In a further aspect of the invention the alpha-WOLF 27 allele encodes for a protein having an amino acid sequence which in order of increased preference has at least 95%, 95.3%, 95.5%, 95.8%, 96%, 96.3%, 96.5%, 96.8%, 97%, 97.3%, 97.5%, 97.8%, 98%, 98.3%, 98.5%, 98.8%, 99%, 99.1%, 99.2%, 99.3%, 99.4%, 99.5%, 99.6%, 99.7%, 99.8%, 99.9%, 100% sequence identity to SEQ ID NO: 13.

In a further aspect of the invention the alpha-WOLF 27 allele encodes for a protein having an amino acid sequence which in order of increased preference has at least 95%, 95.3%, 95.5%, 95.8%, 96%, 96.3%, 96.5%, 96.8%, 97%, 97.3%, 97.5%, 97.8%, 98%, 98.3%, 98.5%, 98.8%, 99%, 99.1%, 99.2%, 99.3%, 99.4%, 99.5%, 99.6%, 99.7%, 99.8%, 99.9%, 100% sequence similarity to SEQ ID NO: 13.

The alpha-WOLF 27 allele when present in a spinach plant confers complete resistance to at least one of the 17 officially recognized *Peronospora farinosa* f. sp. *spinaciae* races. In a further embodiment, the alpha-WOLF 27 allele when present in a spinach plant confers complete resistance to at least two of the 17 officially recognized *Peronospora farinosa* f. sp. *spinaciae* races. In a further embodiment, the alpha-WOLF 27 allele when present in a spinach plant confers complete resistance in order of increased preference to at least two, three, four, five, six, seven, eight, nine, ten, eleven, twelve, thirteen, fourteen, fifteen, sixteen or all of the seventeen officially recognized *Peronospora farinosa* f. sp. *spinaciae* races.

The alpha-WOLF 27 allele when homozygously present in a spinach plant confers complete resistance to at least the officially recognized *Peronospora farinosa* f. sp. *spinaciae* races Pfs: 7, Pfs: 8, Pfs: 9, Pfs: 11, Pfs: 12, Pfs: 13, Pfs: 14, Pfs: 15, Pfs: 17. More in particular, the alpha-WOLF 27 allele when homozygously present in a spinach plant confers complete resistance to at least the officially recognized *Peronospora farinosa* f. sp. *spinaciae* races Pfs: 1, Pfs: 2, Pfs: 3, Pfs: 4, Pfs: 5, Pfs: 6, Pfs: 7, Pfs: 8, Pfs: 9, Pfs: 11, Pfs: 12, Pfs: 13, Pfs: 14, Pfs: 15, Pfs: 17 (see Table 1).

The resistance of a spinach plant against one or more races of *Peronospora farinosa* f. sp. *spinaciae* can be determined using a seedling test. Herein, a seedling test is defined as a test wherein spinach plants are planted in trays containing growth medium, fertilized twice a week after seedling emergence. Plants are inoculated at the first true leaf stage with a sporangial suspension having a concentration of approximately $2.5 \times 10^5$/ml of one of the pathogenic races of *Peronospora farinosa* f. sp. *spinaciae* or isolates to be tested. Thirty plants per race are tested. The inoculated plants are placed in a dew chamber at 18° C. with 100% relative humidity for a 24 h period, and then moved to a growth chamber at 18° C. with a 12 h photoperiod for 6 days. After 6 days, the plants are returned to the dew chamber for 24 h to induce sporulation, and subsequently scored for a disease reaction.

As used herein, a plant is completely resistant against a *Peronospora farinosa* f. sp. *spinaciae* race when a plant shows no symptoms in the seedling test described herein.

As used herein, a plant is intermediately resistant against a *Peronospora farinosa* f. sp. *spinaciae* race when a plant shows only symptoms of chlorosis, or sporulation occurring only on the tips of the cotyledons in the seedling test described herein.

As used herein, a plant is susceptible to an isolate of a *Peronospora farinosa* f. sp. *spinaciae* race when a plant shows more than only symptoms of chlorosis, or when sporulation occurs on area larger than only the tips of the cotyledons in the seedling test described herein.

Another aspect of the invention relates to a spinach plant, which may comprise the alpha-WOLF 27 allele of invention, of which a representative sample of seed was deposited with the NCIMB under accession number NCIMB 43668.

In a further embodiment the plant of the invention which may comprise the alpha-WOLF 27 allele is an agronomically elite spinach plant. In the context of this invention an agronomically elite spinach plant is a plant having a genotype that results into an accumulation of distinguishable and desirable agronomic traits which allow a producer to harvest a product of commercial significance, preferably the agronomically elite spinach plant which may comprise the alpha-WOLF 27 allele is a plant of an inbred line or a hybrid.

As used herein, a plant of an inbred line is a plant of a population of plants that is the result of three or more rounds of selfing, or backcrossing; or which plant is a double haploid. An inbred line may e.g. be a parent line used for the production of a commercial hybrid.

As used herein, a hybrid plant is a plant which is the result of a cross between two different plants having different genotypes. More in particular, a hybrid plant is the result of a cross between plants of two different inbred lines, such a hybrid plant may e.g. be a plant of an $F_1$ hybrid variety.

A plant carrying the alpha-WOLF 27 allele in heterozygous form may further comprise a beta-WOLF 0 allele as e.g. present in variety Viroflay wherein the beta-WOLF 0 allele does not confer any resistance to downy mildew. However, a plant heterozygous for the alpha-WOLF 27 allele may further comprise an allele of the alpha/beta-WOLF gene that does provide resistance to downy mildew. Preferably, such an allele would complement the alpha-WOLF 27 allele such that the spinach plant will be at least intermediately resistant to one or more other races to which the alpha-WOLF 27 allele does not provide resistance. Most preferably the other allele of the alpha/beta-WOLF gene complements the alpha-WOLF 27 allele such that the plant is resistant to *Peronospora farinosa* f. sp. *spinaciae* races Pfs:1 to Pfs:17. In one embodiment such a plant is an agronomically elite plant.

Alternatively, the resistance profile of a plant carrying the alpha-WOLF 27 allele is complemented by a resistance conferring allele of a totally different gene. Examples of such genes are e.g. DMR1 as described in U.S. Pat. No. 8,354,570, DMR6 as described in U.S. Pat. No. 9,121,029 and p10 as described in U.S. Pat. No. 10,226,016.

The invention thus relates to a spinach plant carrying the alpha-WOLF 27 allele and which may further comprise a genetic determinant resulting in resistance against *Peronospora farinosa* f. sp. *spinaciae* races Pfs:1 to Pfs:17. The genetic determinant can be another resistance conferring alpha/beta-WOLF allele or a resistance conferring allele of a totally different gene.

The invention further relates to propagation material which may comprise the alpha-WOLF 27 allele. In one embodiment, the propagation material is suitable for sexual reproduction. Such propagation material may comprise for example a microspore, pollen, ovary, ovule, embryo sac and egg cell. In another embodiment, the propagation material is suitable for vegetative reproduction. Such propagation material may comprise for example a cutting, root, stem, cell, protoplast, and a tissue culture of regenerable cells. A part of the plant that is suitable for preparing tissue cultures is in particular a leaf, pollen, an embryo, a cotyledon, a hypocotyl, a meristematic cell, a root tip, an anther, a flower, a seed and a stem.

The invention furthermore relates to a cell of a spinach plant which may comprise the alpha-WOLF 27 allele. Such a cell may be either in isolated form or may be part of the complete plant or parts thereof and then still constitutes a cell of the invention because such a cell harbors the alpha-WOLF 27 allele that confers resistance to downy mildew. Each cell of a plant of the invention carries the genetic information that confers resistance to *Peronospora farinosa* f. sp. *spinaciae*. Such a cell of the invention may also be a regenerable cell that may be used to regenerate a new plant which may comprise the allele of the invention.

Yet another aspect of the invention relates to a method for making a hybrid spinach seed which may comprise crossing a first parent spinach plant with a second parent spinach plant and harvesting the resultant hybrid spinach seed, wherein said first and/or second parent spinach plant may comprise the alpha-WOLF 27 allele. In particular embodiment, the first and/or second parent plant is a plant of an inbred line as defined herein.

The invention further relates to a hybrid spinach plant grown from seed produced by crossing a first parent spinach plant with a second parent spinach plant and harvesting the resultant hybrid spinach seed, wherein said first and/or second parent spinach plant may comprise the alpha-WOLF 27 allele.

Determining the genomic DNA or coding DNA sequence of at least part of a WOLF gene in the genome of a spinach plant may be performed using any suitable molecular biological method known in the art, including but not limited to (genomic) PCR amplification followed by Sanger sequencing, whole-genome-sequencing, transcriptome sequencing, sequence-specific target capture followed by next-generation sequencing (using, for example, the xGen® target capture system of Integrated DNA Technologies), specific amplification of LRR-domain-comprising gene sequences (using, for example, the RenSeq methodology, as described in U.S. patent application Ser. No. 14/627,116, and in Jupe et al., 2013, Plant J. 76: 530-544) followed by sequencing, etcetera.

In one embodiment the invention relates to a method for identifying a plant carrying the alpha-WOLF 27 allele may comprise determining the DNA sequence coding for the LRR domain as defined herein.

In a further embodiment of the method the LRR domain of the alpha-WOLF 27 allele is determined by using a primer pair to amplify the genomic DNA region of the LRR domain. The forward primer is preferably a nucleic acid molecule having the sequence of SEQ ID NO: 4 and the reverse primer is preferably a nucleic acid molecule having the sequence of SEQ ID NO: 5.

Another aspect of the invention relates to a method for producing a spinach plant which may comprise resistance to *Peronospora farinosa* f. sp. *spinaciae* which may comprise: (a) crossing a plant which may comprise the alpha-WOLF 27 allele, with another plant; (b) optionally performing one or more rounds of selfing and/or crossing; (c) optionally selecting after each round of selfing or crossing for a plant that may comprise the alpha-WOLF 27 allele.

Selecting a plant which may comprise the alpha-WOLF 27 allele can be done by determining the presence of the DNA sequence of the NBS-LRR domain of the allele having in order of increased preference 97%, 97.3%, 97.5%, 97.8%, 98%, 98.3%, 98.5%, 98.8%, 99%, 99.1%, 99.2%, 99.3%, 99.4%, 99.5%, 99.6%, 99.7%, 99.8%, 99.9%, 100% sequence identity to SEQ ID NO: 9.

In another embodiment, selecting a plant which may comprise the alpha-WOLF 27 allele can be done by determining the presence the coding sequence of the entire allele.

Alternatively, the presence of the alpha-WOLF 27 allele can be determined phenotypically by assaying a plant in a disease test, for example the test as described herein.

The invention further relates to the use of a spinach plant carrying the alpha-WOLF 27 allele in breeding to confer resistance against *Peronospora farinosa* f. sp. *spinaciae*. The invention also relates to a breeding method for the development of spinach plants carrying the alpha-WOLF 27 allele of the invention wherein germplasm which may comprise said allele is used. Seed capable of growing into a plant which may comprise the allele of the invention and being representative for the germplasm was deposited with the NCIMB under accession number NCIMB 43668.

In another aspect, the invention relates to a method for the production of a spinach plant which may comprise alpha-WOLF 27 allele, which method may comprise: (a) crossing a plant which may comprise the allele with another plant; (b) optionally selecting for plants which may comprise said allele in the F1; (c) optionally backcrossing the resulting F1 with the preferred parent and selecting for plants that have the said allele in the BC1F1; (d) optionally performing one or more additional rounds of selfing, crossing, and/or backcrossing, and subsequently selecting for a plant which may comprise the said allele or shows the resistance profile corresponding to said allele. The invention also encompasses a spinach plant produced by this method.

The invention also relates to a harvested leaf of a spinach plant of the invention, to a food product which may comprise a harvested leaf of a spinach plant of the invention, either in natural or in processed form.

Spinach leaves are sold in packaged form, including without limitation as pre-packaged spinach leaves or as processed in a salad which may comprise said leaves. Mention of such a package is e.g. made in U.S. Pat. No. 5,523,136, which provides packaging film, and packages from such packaging film, including such packaging containing leafy produce, and methods for making and using such packaging film and packages, which are suitable for use with the spinach leaves of the invention. Thus, the invention comprehends the use of and methods for making and using the leaves of the spinach plant of the invention, as well as leaves of spinach plants derived from the invention.

The invention further relates to a container which may comprise one or more plants of the invention, or one or more spinach plants derived from a plant of the invention, in a growth substrate for harvest of leaves from the plant, in a domestic environment. This way the consumer may pick very fresh leaves for use in salads, when the plant is in a ready-to-harvest condition.

The invention also relates to the use of a spinach plant, of which representative seed was deposited with the NCIMB under accession number NCIMB 43668, in the production of a spinach plant which may comprise the alpha-WOLF 27 allele.

In a further embodiment the said spinach plant is a hybrid, doubled haploid, or inbred spinach plant Another aspect of the invention is the use of a cell which may comprise the alpha-WOLF 27 allele for the production of a spinach plant showing resistance to *Peronospora farinosa* f. sp. *spinaciae*.

In one embodiment the invention relates to an allele designated alpha-WOLF 27 which when present in a spinach plant homozygously confers complete resistance to at least *Peronospora farinosa* f. sp. *spinaciae* race Pfs: 7, Pfs: 8, Pfs: 9, Pfs: 11, Pfs: 12, Pfs: 13, Pfs: 14, Pfs: 15, Pfs: 17. In another embodiment, alpha-WOLF 27 when present in a spinach plant homozygously confers complete resistance to at least *Peronospora farinosa* f. sp. *spinaciae* race Pfs: 1, Pfs: 2, Pfs: 3, Pfs: 4, Pfs: 5, Pfs: 6, Pfs: 7, Pfs: 8, Pfs: 9, Pfs: 11, Pfs: 12, Pfs: 13, Pfs: 14, Pfs: 15, Pfs: 17. In both embodiments, the protein encoded by said allele is a CC-NBS-LRR protein that may comprise in its amino acid sequence: a) the motif "MAEIGYSVC" at its N-terminus; and b) the motif "KWMCLR"; and wherein the LRR domain of the protein has in order of increased preference at least 95%, 95.5%, 96%, 96.5%, 97%, 97.5%, 98%, 98.5%, 99%, 99.5%, 100% sequence identity to SEQ ID NO: 10.

In another embodiment, the invention relates to an allele designated alpha-WOLF 27 which when present in a spinach plant homozygously confers complete resistance to at least *Peronospora farinosa* f. sp. *spinaciae* race Pfs: 7, Pfs: 8, Pfs: 9, Pfs: 11, Pfs: 12, Pfs: 13, Pfs: 14, Pfs: 15, Pfs: 17 or Pfs: 1, Pfs: 2, Pfs: 3, Pfs: 4, Pfs: 5, Pfs: 6, Pfs: 7, Pfs: 8, Pfs: 9, Pfs: 11, Pfs: 12, Pfs: 13, Pfs: 14, Pfs: 15, Pfs: 17, wherein the protein encoded by said allele is a CC-NBS-LRR protein that may comprise in its amino acid sequence: a) the motif "MAEIGYSVC" at its N-terminus; and b) the motif "KWMCLR"; and wherein the LRR domain of the protein has in order of increased preference at least 99.5% sequence identity to SEQ ID NO: 10.

In another embodiment the invention relates to an allele designated alpha-WOLF 27 which when present in a spinach plant homozygously confers complete resistance to at least *Peronospora farinosa* f. sp. *spinaciae* race Pfs: 7, Pfs: 8, Pfs: 9, Pfs: 11, Pfs: 12, Pfs: 13, Pfs: 14, Pfs: 15, Pfs: 17 or Pfs: 1, Pfs: 2, Pfs: 3, Pfs: 4, Pfs: 5, Pfs: 6, Pfs: 7, Pfs: 8, Pfs: 9, Pfs: 11, Pfs: 12, Pfs: 13, Pfs: 14, Pfs: 15, Pfs: 17, wherein the protein encoded by said allele is a CC-NBS-LRR protein that may comprise in its amino acid sequence: a) the motif "MAEIGYSVC" at its N-terminus; and b) the motif "KWMCLR"; and wherein the LRR domain of the protein has in order of increased preference at least 95%, 95.5%, 96%, 96.5%, 97%, 97.5%, 98%, 98.5%, 99%, 99.5%, 100% sequence identity to SEQ ID NO: 10, and wherein the DNA sequence of the LRR domain in order of increased preference has at least 97%, 97.3%, 97.5%, 97.8%, 98%, 98.3%, 98.5%, 98.8%, 99%, 99.3%, 99.5%, 99.8%, 100% sequence identity to SEQ ID NO: 9.

In another embodiment the invention relates to an allele designated alpha-WOLF 27 which when present in a spinach plant homozygously confers complete resistance to at least *Peronospora farinosa* f. sp. *spinaciae* race Pfs: 7, Pfs: 8, Pfs: 9, Pfs: 11, Pfs: 12, Pfs: 13, Pfs: 14, Pfs: 15, Pfs: 17 or Pfs: 1, Pfs: 2, Pfs: 3, Pfs: 4, Pfs: 5, Pfs: 6, Pfs: 7, Pfs: 8, Pfs: 9, Pfs: 11, Pfs: 12, Pfs: 13, Pfs: 14, Pfs: 15, Pfs: 17, wherein the protein encoded by said allele is a CC-NBS-LRR protein that may comprise in its amino acid sequence: a) the motif "MAEIGYSVC" at its N-terminus; and b) the motif "KWMCLR"; and wherein the DNA sequence of the LRR domain in order of increased preference has at least 97%, 97.3%, 97.5%, 97.8%, 98%, 98.3%, 98.5%, 98.8%, 99%, 99.3%, 99.5%, 99.8%, 100% sequence identity to SEQ ID NO: 9.

In a further embodiment the invention relates to a spinach plant which may comprise an allele designated alpha-WOLF 27 which when present in a spinach plant homozygously confers complete resistance to at least *Peronospora farinosa* f. sp. *spinaciae* race Pfs: 7, Pfs: 8, Pfs: 9, Pfs: 11, Pfs: 12, Pfs: 13, Pfs: 14, Pfs: 15, Pfs: 17. In another embodiment, the invention relates to a spinach plant which may comprise an alpha-WOLF 27 allele which when present in a spinach plant homozygously confers complete resistance to at least *Peronospora farinosa* f. sp. *spinaciae* race Pfs: 1, Pfs: 2, Pfs: 3, Pfs: 4, Pfs: 5, Pfs: 6, Pfs: 7, Pfs: 8, Pfs: 9, Pfs: 11, Pfs: 12, Pfs: 13, Pfs: 14, Pfs: 15, Pfs: 17. In both embodiments, the protein encoded by said allele is a CC-NBS-LRR protein that may comprise in its amino acid sequence: a) the motif "MAEIGYSVC" at its N-terminus; and b) the motif "KWMCLR"; and wherein the LRR domain of the protein has in order of increased preference at least 95%, 95.3%, 95.5%, 95.8%, 96%, 96.3%, 96.5%, 96.8%, 97%, 97.3%, 97.5%, 97.8%, 98%, 98.3%, 98.5%, 98.8%, 99%, 99.3%, 99.5%, 99.8%, 100% sequence identity to SEQ ID NO: 10. Preferably this spinach plant is an agronomically elite spinach plant.

In a further embodiment, the invention relates to a spinach plant which may comprise an allele designated alpha-WOLF 27 which when present in a spinach plant homozygously confers complete resistance to at least *Peronospora farinosa* f. sp. *spinaciae* race Pfs: 7, Pfs: 8, Pfs: 9, Pfs: 11, Pfs: 12, Pfs: 13, Pfs: 14, Pfs: 15, Pfs: 17 or Pfs: 1, Pfs: 2, Pfs: 3, Pfs: 4, Pfs: 5, Pfs: 6, Pfs: 7, Pfs: 8, Pfs: 9, Pfs: 11, Pfs: 12, Pfs: 13, Pfs: 14, Pfs: 15, Pfs: 17, wherein the protein encoded by said allele is a CC-NBS-LRR protein that may comprise in its amino acid sequence: a) the motif "MAEIGYSVC"at its N-terminus; and b) the motif "KWMCLR"; and wherein the LRR domain of the protein has in order of increased preference at least 99.8% sequence identity to SEQ ID NO: 10. Preferably this spinach plant is an agronomically elite spinach plant.

In a further embodiment, the invention relates to a spinach plant which may comprise an allele designated alpha-WOLF 27 which when present in a spinach plant homozygously confers complete resistance to at least *Peronospora farinosa* f. sp. *spinaciae* race Pfs: 7, Pfs: 8, Pfs: 9, Pfs: 11, Pfs: 12, Pfs: 13, Pfs: 14, Pfs: 15, Pfs: 17 or Pfs: 1, Pfs: 2, Pfs: 3, Pfs: 4, Pfs: 5, Pfs: 6, Pfs: 7, Pfs: 8, Pfs: 9, Pfs: 11, Pfs: 12, Pfs: 13, Pfs: 14, Pfs: 15, Pfs: 17, wherein the protein encoded by said allele is a CC-NBS-LRR protein that may comprise in its amino acid sequence: a) the motif "MAEIGYSVC" at its N-terminus; and b) the motif "KWMCLR"; and wherein the LRR domain of the protein has in order of increased preference at least 95%, 95.3%, 95.5%, 95.8%, 96%, 96.3%, 96.5%, 96.8%, 97%, 97.3%, 97.5%, 97.8%, 98%, 98.3%, 98.5%, 98.8%, 99%, 99.3%, 99.5%, 99.8%, 100% sequence identity to SEQ ID NO: 10, and wherein the DNA sequence of the LRR domain in order of increased preference has at least 97%, 97.3%, 97.5%, 97.8%, 98%, 98.3%, 98.5%, 98.8%, 99%, 99.3%, 99.5%, 99.8%, 100% sequence identity to SEQ ID NO: 9. Preferably this spinach plant is an agronomically elite spinach plant.

In a further embodiment, the invention relates to a spinach plant which may comprise an allele designated alpha-WOLF 27 which when present in a spinach plant homozygously confers complete resistance to at least *Peronospora farinosa* f. sp. *spinaciae* race Pfs: 7, Pfs: 8, Pfs: 9, Pfs: 11, Pfs: 12, Pfs: 13, Pfs: 14, Pfs: 15, Pfs: 17 or Pfs: 1, Pfs: 2, Pfs: 3, Pfs: 4, Pfs: 5, Pfs: 6, Pfs: 7, Pfs: 8, Pfs: 9, Pfs: 11, Pfs: 12, Pfs: 13, Pfs: 14, Pfs: 15, Pfs: 17, wherein the protein encoded by said allele is a CC-NBS-LRR protein that may comprise in its amino acid sequence: a) the motif "MAEIGYSVC" at its N-terminus; and b) the motif "KWMCLR"; and wherein the DNA sequence of the LRR domain in order of increased preference has at least 97%, 97.3%, 97.5%, 97.8%, 98%, 98.3%, 98.5%, 98.8%, 99%, 99.3%, 99.5%, 99.8%, 100% sequence identity to SEQ ID NO: 9. Preferably this spinach plant is an agronomically elite spinach plant.

RESISTANCE INFORMATION

TABLE 1

Resistance profile conferred by the alpha-WOLF 27 allele when homozygously present in a spinach plant.
alpha-WOLF 27 resistance profile

| *Peronospora farinosa* f. sp. *spinaciae* race | Resistance score |
| --- | --- |
| Pfs: 1 | − |
| Pfs: 2 | − |
| Pfs: 3 | − |
| Pfs: 4 | − |
| Pfs: 5 | − |
| Pfs: 6 | − |
| Pfs: 7 | − |
| Pfs: 8 | − |
| Pfs: 9 | − |
| Pfs: 10 | nt |
| Pfs: 11 | − |
| Pfs: 12 | − |
| Pfs: 13 | − |
| Pfs: 14 | − |
| Pfs: 15 | − |
| Pfs: 16 | nt |
| Pfs: 17 | − |

A "−" means complete resistance against a particular downy mildew race; "(−)" means intermediate resistance against a particular downy mildew race; "+" means that the allele confers no resistance and would cause a plant only carrying the alpha-WOLF 27 allele to be fully susceptible for that particular downy mildew race; "nt" means that it has not been tested against that isolate.

SEQUENCE INFORMATION

TABLE 2

| Sequence information. | |
| --- | --- |
| SEQ ID NO: 1: | MAEIGYSVC |
| SEQ ID NO: 2: | KWMCLR |
| SEQ ID NO: 3: | HVGCVVDR |

TABLE 2-continued

| Sequence information. | |
| --- | --- |
| SEQ ID NO: 4:<br>Forward primer<br>LRR domain<br>(Alpha) | ACAAGTGGATGTGTCTTAGG |
| SEQ ID NO: 5:<br>Reverse primer<br>LRR domain<br>(Alpha) | TTCGCCCTCATCTTCCTGG |
| SEQ ID NO: 6:<br>Forward primer<br>LRR domain<br>(Beta) | TCACGTGGGTTGTGTTGT |
| SEQ ID NO: 7:<br>Amplicon of<br>LRR domain of<br>the beta-WOLF 0<br>allele<br>(Viroflay) | TCACGGGGTTGTGTTGTCGA<br>TAGAGATCCAGAAATAGTCT<br>TTTTATGTAGCAATAAGATT<br>CGTTCGTATATTAGCGGTCG<br>CTGCATAAAGAATCCGGTGG<br>ATTCACAAATAGACAACTGG<br>ATGTGCCTTAGGGTGTTGGA<br>CTTGTCAGATTCATGTGTTA<br>AAGATTTGTCTGATTCAATA<br>GGTAAGCTGCTGCACTTAAG<br>GTATCTTAACCTCTCTTCTA<br>ATATAAAGTTGGAGATAATC<br>CCTGATGCAATTACAAGACT<br>GCATAACTTGCAGACACTAC<br>TTTTAGAAGATTGCAGAAGT<br>TTAAAGGAGTTGCCAAAAGA<br>TTTTTGCAAATTGGTCAAAC<br>TGAGGCACTTGGAATTACAG<br>GGTTGTCATGATTTGATTGG<br>TATGTCATTTGGAATGGATA<br>AGCTAACTAGTCTTAGAATA<br>CTACCAAACATTGTGGTGGG<br>TAGGAAGGAACAAAGTGTTG<br>ATGATGAGCTGAAAGCCCTA<br>AAAGGCCTCACCGAGATAAA<br>AGGCTCCATTGATATCACAA<br>TCTATTCAAAATATAGAAGA<br>GTTGAAGGCATGAATGGCAC<br>AGGAGGAGGAGCTGGGTATT<br>TGAAGAGCATGAAACATCTC<br>ACGGGGGTTAATATTACATT<br>TGATGAAGGTGGATGTGTTA<br>ACCCTGAAGCTGTGTATTTG<br>AAGAGCATGAAACATCTCAC<br>GAGGGTTATTATTATATTTG<br>ATTATAAAGGTGGATGTGTT<br>AACCCTGAAGCTGTGTTGGC<br>AACCCTAGAGCCACCTTCAA<br>ATATCAAGA<br>GGTTAGAGATGTGGCATTAC<br>AGTGGTACAACAATTCCAGT<br>ATGGGGAAGAGCAGAGATTA<br>ATTGGGCAATCTCCCTCTCA<br>CATCTTGTCGACATCACGCT<br>TGAAGATTGTTACAATTTGC<br>AGGAGATGCCAGTGCTGAGT<br>AAACTGCCTCATTTGAAATC<br>ACTGGAACTTACAGAGTTGG<br>ATAACTTAGAGTACATGGAG<br>AGTAGAAGCAGCAGCAGTAG<br>CAGTGACACAGAAGCAGCAA<br>CACCAGAATTACCAACATTC<br>TTCCCTTCCCTTGAAAAACT<br>TACACTTTGGCGTCTGGACA<br>AGTTGAAGGGTTTTGGGAAC<br>AGGAGATCGAGTAGTTTTCC<br>CCGCCTCTCTAAATTGGAAA<br>TCTGGAAATGTCCAGATCTA<br>ACGTCATTTCCTTCTTGTCC<br>AAGCCTTGAAGAGTTGGAAT<br>TGAAAGAAAACAATGAAGCG<br>TTGCAAATAATAGTAAAAAT |

TABLE 2-continued

Sequence information.

| | |
|---|---|
| | AACAACAACAAGAGGTAAAG<br>AAGAAAAAGAAGAAGACAAG<br>AATGCTGGTGTTGGAAATTC<br>ACAAGATGATGACAATGTCA<br>AATTATGGAAGGTGGAAATA<br>GACAATCTGGGTTATCTCAA<br>ATCACTGCCCACAAATTGTC<br>TGACTCACCTCGACCTTACA<br>ATAAGTGATTCCAAGGAGGG<br>GGAGGGTGAATGGGAAGTTG<br>GGGATGCATTTCAGAAGTGT<br>GTATCTTCTTTGAGAAGCCT<br>CACCATAATCGGAAATCACG<br>GAATAAATAAAGTGAAGAGA<br>CTGTCTGGAAGAACAGGGTT<br>GGAGCATTTCACTCTGTTGG<br>AATCACTCAAACTTTCAGAT<br>ATAGAAGACCAGGAAGATGA<br>GGGCGAA |
| SEQ ID NO: 8:<br>Amino acid<br>sequence<br>encoded by<br>amplicon of LRR<br>domain Beta<br>Wolf 0 (Viroflay) | HVGCVVDRDPEIVFLCSNKI<br>RSYISGRCIKNPVDSQIDNW<br>MCLRVLDLSDSCVKDLSDSI<br>GKLLHLRYLNLSSNIKLEII<br>PDAITRLHNLQTLLLEDCRS<br>LKELPKDFCKLVKLRHLELQ<br>GCHDLIGMSFGMDKLTSLRI<br>LPNIVVGRKEQSVDDELKAL<br>KGLTEIKGSIDITIYSKYRR<br>VEGMNGTGGGAGYLKSMKHL<br>TGVNITFDEGGCVNPEAVYL<br>KSMKHLTRVIIIFDYKGGCV<br>NPEAVLATLEPPSNIKRLEM<br>WHYSGTTIPVWGRAEINWAI<br>SLSHLVDITLEDCYNLQEMP<br>VLSKLPHLKSLELTELDNLE<br>YMESRSSSSSDTEAATPEL<br>PTFFPSLEKLTLWRLDKLKG<br>FGNRRSSSFPRLSKLEIWKC<br>PDLTSFPSCPSLEELELKEN<br>NEALQIIVKITTTRGKEEKE<br>EDKNAGVGNSQDDDNVKLWK<br>VEIDNLGYLKSLPTNCLTHL<br>DLTISDSKEGEGEWEVGDAF<br>QKCVSSLRSLTIIGNHGINK<br>VKRLSGRTGLEHFTLLESLK<br>LSDIEDQEDEGE |
| SEQ ID NO: 9:<br>Amplicon of<br>LRR domain of<br>the alpha-WOLF<br>27 allele | TGGATGTGTCTTAGGATGTT<br>GGACTTGTCAAGGCCGGATG<br>TTAAAAATTTGCCTAATTCA<br>ATAGGTAAATTGTTGCACTT<br>GAGGTATCTTAACCTGTCTT<br>GTAATGATGATCTGTTGATA<br>CTCCCTGATGCAATTACAAG<br>ACTGCATAATTTGCAGACAC<br>TGCTTTTAAAAGATTGCGGA<br>AGTTTAAAGGAGTTGCCAAA<br>AGATTTTTGCAAATTGGTCA<br>AACTGAGACACTTGGATTTA<br>AGGTATTGTTGGCGTTTGAT<br>TGGTATGCCATTGGGAATGG<br>ATATGCTAACTAGTCTTAGA<br>GTACTGCCATACTTTGTGGT<br>GGGTAGGAAGAAACAAAGTG<br>TTGATGATGAGCTGAAAGCC<br>CTTAAAGGCCTCACCGAGAT<br>AAAAGGCTCCATTAATATCA<br>AAATCTGTGAAAATTATAGA<br>ATAGTTGAAGGCATGAATGA<br>CACAGGAGGAGCTGGGTATT<br>TGAAGAGCATGAAACATCTC<br>ACGGGGTTGATATTCATT<br>TGATGGTGGATGTGTTAACC<br>CTGAAGCTGTGTTGGAAACC<br>CTAGAGCCACCTTCAAATAT<br>CAAGAGGTTATCTATAGATA<br>ATTACGATGGTACAACAATT | |
| | CCAGTATGGGGAAGAGCAGA<br>GATTAATTGGGCAATCTCCC<br>TCTCACATCTTGTCGACATT<br>TGGTTTTGTGGTTGTAGTAA<br>TTTGCAGGAGATGCCAGTGC<br>TGAGTAAACTGCCTCATTTG<br>AAATCA<br>CTGAATCTTTTTAAGTTTTG<br>TAAGTTAGAGTACATGGAGA<br>GTAGAAGCAGCAGCAGTAGC<br>AGTGACACAGAAGCAGCAAC<br>ACCAGAATTACCAACATTCT<br>TCCCTTCCCTTGAAAAACTT<br>ACACTTTGGTATCTGGAAAA<br>GTTGAAGGGTTTGGGGAACA<br>GGAGATCGAGTAGTTTTCCC<br>CGCCTCTCTGAATTGGAAAT<br>CTGGGAATGCCCAGATCTAA<br>CGTGGTTTCCTCCTTGTCCA<br>AGCCTTAAAACGTTGAAATT<br>GGAAAAAAACAATGAAGCGT<br>TGCAAATAATAGTAAAAATA<br>ACAACAACAAGAGGTAAAG<br>AGAAAAAGAAGAAGACAAGA<br>ATGCTGGTGTTGGAAATTCA<br>CAAGATGATGACAATGTCAA<br>ATTACGGAAGGCGGAAATAG<br>ACAATCTGGGTTATCTCAAA<br>TCACTGCCCACAAATTGTCT<br>GACTCACCTCGACATTACAA<br>TAAGAGATTCCAAGGAGGGG<br>GAGGGTGAATGGGAAGTTGG<br>GGAGGCATTTCAGAAGTGTG<br>TATCTTCTTTGAGAAGCTCA<br>GCATAATCGGAAATCACGG<br>AATAAATAAAGTGAAGAGAC<br>TGTCTGGAAGAACAGGGTTG<br>GAGCATTTCACTCTGTTGGA<br>CTCACTCAAATTTTCAAAGA<br>TAGAAGACCAGGAAGATGAG<br>GGCGAA |
| SEQ ID NO: 10:<br>Amino acid<br>sequence<br>encoded by<br>amplicon of LRR<br>domain of alpha-<br>WOLF27 | WMCLRMLDLSRPDVKNLPNS<br>IGKLLHLRYLNLSCNDDLLI<br>LPDAITRLHNLQTLLLKDCG<br>SLKELPKDFCKLVKLRHLDL<br>RYCWRLIGMPLGMDMLTSLR<br>VLPYFVVGRKKQSVDDELKA<br>LKGLTEIKGSINIKICENYR<br>IVEGMNDTGGAGYLKSMKHL<br>TGVDITFDGGCVNPEAVLET<br>LEPPSNIKRLSIDNYDGTTI<br>PVWGRAEINWAISLSHLVDI<br>WFCGCSNLQEMPVLSKLPHL<br>KSLNLFKFCKLEYMESRSSS<br>SSSDTEAATPELPTFFPSLE<br>KLTLWYLEKLKGLGNRRSSS<br>FPRLSELEIWECPDLTWFPP<br>CPSLKTLKLEKNNEALQIIV<br>KITTTRGKEEKEEDKNAGVG<br>NSQDDDNVKLRKAEIDNLGY<br>LKSLPTNCLTHLDITIRDSK<br>EGEGEWEVGEAFQKCVSSLR<br>KLSIIGNHGINKVKRLSGRT<br>GLEHFTLLDSLKFSKIEDQE<br>DEGE |
| SEQ ID NO: 11:<br>genomic DNA<br>sequence of the<br>alpha-WOLF 27<br>allele | GTTCTGTTTTTTATGGCACA<br>GATATCCCTCATTTGCAGCT<br>CTACTTCTACAAACATCTTT<br>CATTCTTCGTTTTCCTTTT<br>GATTCATGTAACAGTTGAAC<br>CTTCTTTCATGACTGATATA<br>GAATCAGGCAGCTACTTCAC<br>TACTTCTATGTTGATCTTAT<br>TTTGTAATAAACTTTGATAG<br>ATTGAATAAAGGTTGTTTGC<br>AGTGACTTCTTAAGATGTGA |

TABLE 2-continued

Sequence information.

TTAGAAGTCCATAATCACTT
TAAGGTAGTTTTTCTTTACA
TGATTAAGGTTTTTCCGAGG
CCTTTCTATTGCTTTGTTGG
TTACTGTCATGACATATGGT
TTTTCTTTGCTTCTTATATC
ATATGGTCCTCACTCAATTT
TTTAATATAAAGTTTCTCAT
TGGTTGACTATAATACGTTA
TAGCACCTTATAATATTTTA
TTTAATATACAATTTTATGT
ATTTTACCTTTTTCATATTT
TTTCGTGATCTACCTTCTCA
TATGAGCTACACTAATTTGG
TAGCTGTTTATGCAAATCTT
GTACCAACGGTTGGCTATTT
GCTCAATTTTTTTTTTTTT
TTTTCGAGCTAGTCATTTTA
TGATCATTGAAGTTTGCTCT
TATATTATCATTTATGTATT
TTACCTTTTTTACATTTTTT
TCGTGATCTACCTGCTCATA
TGAGCCACACTAATTTGGTA
GCTGCTTATACAATTCTTGT
ATCAACGGTTGGCTACTTGT
TCAAATATTTTTATTTTTTT
ACGAGTAAGTCATTTTATGA
TCATTGAAGTTGCTCTAATA
TTATCATGGACCTATTAACG
CATGAATAATTAACTCGGTA
GGAATTAGTTTCAAAATAAA
ATTCCCCTCACAAAAAAAAA
AAAAAAAAAAAAAAAAAAAA
TCAGAAAACCAACCTTCTCC
AGTTTACTGTTGTCTAAAGC
CAAAGAGCATGGAATTTTCC
AGTAATCGCAGACCCCAAAT
TCTCTTCTCCAATCGTCCCT
GTCAATTTCAGCAATTGAAT
CAATCGTTGATTTTAGGATT
TGCCGCCAAAAAAATGAAAA
ATCCATGAATTTTAGGGTTC
AAATTTGATCCGTAATTGGG
AAAATTTTCAGCAATTGATC
TTCCAAATCATTCATACTTG
TTTCCAGACTGCAAATGAAA
GGTGCGAACTTTATACTGCA
TTTTGATTTTCCATTACTGT
AATTTATTAAGATGAACTGC
AATTTGCAATTGTTTTATTC
GACTACTCATCTTTAAATCA
AATTGCTAAATTGCTAGCTA
ATTTTCTTATCATATTGCCA
AAAATTTGTTGCTTAAATGA
TTCCATTTCTCTAATTATTT
TTGTTTATTGGTAGATAAA
TAATTAAATATCAGCCCCAT
TAATTGAATATTCAAAGGAA
ATGTATGGTCCAAAAATGGC
GTTTAATAGTCAATGCCGTG
TTTTATGGGTGGTGGAGTA
CTATATGACTGTGTGTGGAC
TTGGAGAAGACTAGAGAGTA
TTGATTATCAAAATATGGAC
CCTGAAAATGAAAATGAAAA
TGATGTTTTACACTTTAAA
ATCGTCAAGAAACAACAATC
CTCTTTAGCAATAGTATTTA
CACGCGTTATTGCACGGAC
TTCAATGCAAATAGTATAAA
TTTACAGTCAAAGTTTTCAT
TCTAAAGCGTAAATAACTTT
CATGAATGAGGACGGTAGT
ATAAGTATAACGTTATGGCC
TACCATTTTCTTATCATATT
CACATAAATTTGTTGCTAAA
AGTTGTTTTACTTGGCTAAA
ATACTTTTGTTCTTATTGGC

AGATAAACATCAGTCCATTA
TTGGCCAACTTGAACATATA
CCTCCAAACAATAATCAATA
ATGTCGATTATGAAGTTTGT
GAATGCAATTTATTATCACT
TTCATTTATAAAATGACTAC
TTGATTAACACATACAATAT
TACCTTTCTCCAAACACCCT
TTCAATTCTGCTTAATCTTG
TTTTCTCATCATCTCTTCAT
CTTTCTGAAAACACAACCCA
ATGGCCGAAATCGGATACTC
GGTTTGTGCGAAACTCATCG
AAGTGATTGGCAGTGAGCTG
ATCAAAGAGATTTGCGACAC
ATGGGGTTACAAATCTCTTC
TTGAGGACCTCAACAAAACT
GTATTGACGGTCAGGAACGT
TCTCATTCAGGCCGGGGTGA
TGCGGGAGCTTACTAGTGAA
CAACAAGGTTTCATTGCAGA
CCTTAAAGATGTTGTTTATG
ATGCTGATGACTTGTTCGAC
AAGTTACTCACTCGTGCTGA
GCGAAAACAGATTGATGGAA
ACGAAATCTCTGAAAAGGTA
CGTCGTTTCTTTTCCTCTAG
TAACAAGATCGGTCAAGCTT
ACTACATGTCTCGTAAGGTT
AAGGAAATTAAGAAGCAGTT
GGATGAAATTGTTGATAGGC
ATACAAAATTTGGGTTTAGT
GCTGAGTTTATACCTGTTTG
TAGGGAAAGGGGGAACGAGA
GGGAAACACGTTCATATATA
GATGTCAAGAATATTCTTGG
GAGGGATAAAGATAAGAATG
ATATCATAGATAGGTTGCTT
AATCGTAATGATAATGAAGC
TTGTAGTTTCCTGACCATAG
TGGGAGCGGGAGGATTGGGA
AAAACTGCTCTTGCCCAACT
TGTGTTCAATGATGAAAGGG
TCAAAATTGAGTTTCATGAT
TTGAGGTATTGGGTTTGTGT
CTCTGATCAAGATGGGGGCC
AATTTGATGTGAAAGAAATC
CTTTGTAAGATTTTAGAGGT
GGTTACTAAGGAGAAAGTTG
ATAATAGTTCCGCATTGGAA
TTGGTACAAAGCCAATTTCA
AGAGAAGTTAAGAGGAAAGA
AGTACTTCCTTGTTCTTGAT
GATGTATGGAACGAGGATCG
TGAGAAGTGGTTTAAATTGG
AAGAGTTGTTAATGTTGGGT
CAAGGGGGAAGCAAGGTTGT
AGTGACCGCACGTTCAGAGA
AGACAGCAAATGTCATAGGG
AAAAGACATTTTTATACACT
GGAATGTTTGTCGCCAGATT
ATTCATGGAGCTTATTTGAA
ATGTCGGCTTTTCAGAAAGG
GCATGAGCAGGAAAACCATG
ACGAACTAGTTGATATTGGG
AAAAAGATTGTTGAAAAATG
TTATAACAATCCACTTGCTA
TAACGGTGGTAGGAAGTCTT
CTTTATGGAGAGGAGATAAG
TAAGTGGCGGTCATTTGAAA
TGAGTGAGTTGGCCAAAATT
GGCAATGGGATAATAAGAT
TTTGTCGATATTGAAGCTCA
GTTACTACAATCTTGCAAAC
TCTTTGAAGAGTTGTTTTAG
TTATTGTGCAGTATTTCCCA
AGGATCATAAAATAGAGAAG
GAGATGTTGATTGACCTTTG

TABLE 2-continued

Sequence information.

```
GATAGCACAAGGATATGTTG
TGCCGTTGGATGGTGGTCAA
AGTATAGAAGATGCTGCCGA
GGAACATTTTGTAATTTTAT
TACGGAGATGTTTCTTTCAA
GATGTAGTGAAGGATGTATA
CGGTGATGTTGATTCTGTTA
AAATCCACGACTTGATGCAC
GATGTCGCCCAAGAAGTGGG
GAGGGAGGAAATATGTGTAG
TGAATGCTAATACAAAGAAC
TTGGGTGATAAAATCCGTCA
TGTACATGGTGATGTCAATA
GATATGCACAAAGAGTCTCT
CTGTGTAGCCATAAGATTCG
TTCGTATATTGGTGGTAATT
GTGAAAAACGTTGGGTGGAT
ACACTAATAGACAACTGGAT
GTGTCTTAGGATGTTGGACT
TGTCAAGGCCGGATGTTAAA
AATTTGCCTAATTCAATAGG
TAAATTGTTGCACTTGAGGT
ATCTTAACCTGTCTTGTAAT
GATGATCTGTTGATACTCCC
TGATGCAATTACAAGACTGC
ATAATTTGCAGACACTGCTT
TTAAAAGATTGCGGAAGTTT
AAAGGAGTTGCCAAAAGATT
TTTGCAAATTGGTCAAACTG
AGACACTTGGATTTAAGGTA
TTGTTGGCGTTTGATTGGTA
TGCCATTGGGAATGGATATG
CTAACTAGTCTTAGAGTACT
GCCATACTTTGTGGTGGGTA
GGAAGAAACAAAGTGTTGAT
GATGAGCTGAAAGCCCTTAA
AGGCCTCACCGAGATAAAAG
GCTCCATTAATATCAAAATC
TGTGAAAATTATAGAATAGT
TGAAGGCATGAATGACACAG
GAGGAGCTGGGTATTTGAAG
AGCATGAAACATCTCACGGG
GGTTGATATTACATTTGATG
GTGGATGTGTTAACCCTGAA
GCTGTGTTGGAAACCCTAGA
GCCACCTTCAAATATCAAGA
GGTTATCTATAGATAATTAC
GATGGTACAACAATTCCAGT
ATGGGGAAGAGCAGAGATTA
ATTGGGCAATCTCCCTCTCA
CATCTTGTCGACATTTGGTT
TTGTGGTTGTAGTAATTTGC
AGGAGATGCCAGTGCTGAGT
AAACTGCCTCATTTGAAATC
ACTGAATCTTTTTAAGTTTT
GTAAGTTAGAGTACATGGAG
AGTAGAAGCAGCAGCAGTAG
CAGTGACACAGAAGCAGCAA
CACCAGAATTACCAACATTC
TTCCCTTCCCTTGAAAAACT
TACACTTTGGTATCTGGAAA
AGTTGAAGGGTTTGGGGAAC
AGGAGATCGAGTAGTTTCC
CCGCCTCTCTGAATTGGAAA
TCTGGGAATGCCCAGATCTA
ACGTGGTTTCCTCCTTGTCC
AAGCCTTAAAACGTTGAAAT
TGGAAAAAACAATGAAGCG
TTGCAAATAATAGTAAAAAT
AACAACAACAAGAGGTAAAG
AAGAAAAAGAAGAAGACAAG
AATGCTGGTGTTGGAAATTC
ACAAGATGATGACAATGTCA
AATTACGGAAGGCGGAAATA
GACAATCGGGTTATCTCAA
ATCACTGCCCACAAATTGTC
TGACTCACCTCGACATTACA
ATAAGAGATTCCAAGGAGGG
```
```
GGAGGGTGAATGGGAAGTTG
GGGAGGCATTTCAGAAGTGT
GTATCTTCTTTGAGAAAGCT
CAGCATAATCGGAAATCACG
GAATAAATAAAGTGAAGAGA
CTGTCTGGAAGAACAGGGTT
GGAGCATTTCACTCTGTTGG
ACTCACTCAAATTTTCAAAG
ATAGAAGACCAGGAAGATGA
GGGCGAAGACAACATCATAT
TCTGGAAATCCTTTCCTCAA
AACCTCCGCAGTTTGGAAAT
TAAAGGCTCTTGCAAAATGA
CAAGTTTGCCCATGGGGATG
CAGTACTTAACCTCCCTCCA
AACCCTCCATCTATCATATT
GTGATGAATTGAATTCCCTT
CCAGAATGGATAAGCAGCTT
ATCATCTCTTCAATCCCTGT
TCATATACAATTGTCCAGCC
CTGAAATCACTACCAGAAGC
AATGAAGAACCTCACCTCCC
TTCAGAGACTTGAGATACAG
CATTGTCCAGACCTAGCTGA
AAGATGCAGAAAACCCAACG
GGGAGGACTATCCCAAAATT
CAACACATCCCCAAAATTGT
AAGTCATTGCAGAAAGTAAT
TTATTCATTTATATTTATTT
TATGCTTAGAATGATATACG
CAGTCGTCCTTTGGTTTCCA
ATCTTGAATTTGGTTTTTGT
TTTCTTTCTTTGTTTCTTTA
TTCAACACCAGTCCATTTAT
GATTGATTCATTAAAAAAAG
GATGGAGTTTTATGGATTTG
AAGAAGACAACGAATTGAGA
TTCCTGGGGTTTTTTTTTTC
GTTGGGGTTGGTTTTCATGT
ATATGTTGCTGATTAAATAC
CAGACTGATGATGATGATGT
GTTTATGGGTTTTAAATCAG
ATTAAATATATGGGAAATGT
AAGTTAATTGGGGATGCACA
TAAGGTGTTTGATGAAATGT
CTATGAGAAATGTTGTTTCT
TGGACTTAGAATGATATACA
CTGTCGTCCTTTGGTTTCCA
ATCTTACATTTGGTTTGTGT
TTTCTTAGTTTGTTTCTTTA
ATCAACACCAGCCCATTTTT
TTTAAACTACCTGCAACTAC
TAATTTTCATTTACCCTGTA
TCTCAGGAAATATGGTAGTA
ATTCTCATTTACTCAACACT
AGCTTGATCCTGAACGCAGC
CAACCTTCAGGTTAGAATCC
GCCTTACTCATCCTTTTGTC
ATGCATTGTTTAAGTTGTT
TTGCTTGCTTGTGTAATCAT
AATTCATAGTATACGATTCA
TCATTCACTATGTCTACAGG
CAAGATATTGGAATTGTTCA
CGATTCCCTGAAGTTTCTTT
GTTTTTGTTGATACCACCAT
ATTGCAGCTTATAGTGACTA
AGTTAATGAATGTTTCCAAA
AAATTAGTCTATATAAATTCT
TCTTCTCTCTCTATTACATA
AACTCTTTTTCTCTTTCTAA
CTTATCATGTTCATGCCTAA
AACTTATACATGCTCACATC
ATTGTTCGTTTGAGCTGACT
TACTTCTGTAAGAGAGCTAT
CTAGTTAACAACTCTTGTAA
CTTTTTATTTGCTAGTCAGA
ACATGGATTGGTGCAAGCAT
GGGAATTTGCTAACACTCTA
```

TABLE 2-continued

Sequence information.

CCAAATCGATTGGAGTTTGG
ACTTAGTTTCACCAGAAGCC
ATACCCGGACACTTACTGGG
GACTGTCAACAAAGCCGCAT
TGTGATGTACTTGGATGTTT
CACGTGCCTGAGGTGCGAGT
TACTTGGAAGGGAAGCGGTT
TATTTAATTGTTTTCCTAAG
TAGATTTTGCTTACAAGCTT
TTACTTTTCACTTGAAAGGG
TTTTTCTTGTTTTAAGCTTT
TCGAATTAGAGTTTTCGGTT
GCATTAAGAGTAGTCGTATT
AGTCTTTTACCTAAGGAAGA
CTCTTTTTTGTAATTTTCAG
ACTATGCAATTCAAGTTTTC
GAGTGTTTTCTTGCTTGTGT
GATTGTGAGTTGGTGAATTC
GTCTTTCATACATTTTGAGA
TTATCAGAAGCTTTATGCTC
CACCGGTAGTCTAGTACCTT
TTCTGTTACTGTACGTGCAG
GGAAGTAATCTGGTACCTTC
TATATATATGGAAAAACATA
CATTATACATTATGCAAAA
TTCTTACAG
GTTAGTTACTTCCTGGAACT
TCATTTACACTTTGTTTTTT
TTGTTCCATTCCCTCGGAAG
ACTATTCCCTCTGAGAAATA
TGTAATGAACTTCTGTATGT
TGCTGTTTGGTTCCTGTTTT
AATCTTCAATTTTCTTGTAT
AGTTACAGCTGCATTTACAA
TGAAGTTTAAGCAGACACTC
TCTTTATATAGTGCTTCTTT
CTGGAGCACCGTTGAGCTGT
CTGTGGTTGATCACCATCTG
CTGCCGAGAGATTCAGCAAT
CGCGTGTTTGATCAGGTAAA
AGTTTTTATGTCAATGTGTT
TTTTTTTTCCGTTGATCAAT
TTATGTCTGTATTCAGATTC
TTATCTTCTTACAGTAGCAT
AACACATTGTTTCTTTCATT
TATGTAAACTGTTTCAAGAT
TACAGAGATGTATGCTTCAG
TCGACATTGATGATAACTTA
AGATAGCATTCCTACAACAG
TTGCAGGCGCATTCTAACTC
CGGCAATTCTAGTTAGGCAA
GAGGAGCATTGCCAATACCT
GCCACCTCTGGGATTTACTA
TACCAGGGTTGAAGTTTATG
GAAGACACCAGCTATGCACA
AGCCTCAAGGGGTCATCCT
ACATAACAAGTTGAACCAAC
CAATTGCTTGTTGGTTCAGT
GGTAATTGGAGCTGAATTTG
GTAGGGATGGCCCATGTTCG
ATCCCCACAACAACAATTGG
GAGGGGACTGGAACCTATCC
ACACGAACTCCGCCCTGAAT
CCGGATTAGTCCTAAGGGTG
AACGGGGTGCTAACACCAAA
AAAAAAAAACATAACAAGTT
GAACCAAACATACTTTGTTT
GAATTGAAGATTTAGTGATT
TCATTTGATCGATTGAGATG
TCTTATTATAAGCGTATATG
CTCTTGGATTTGGCCACTTA
GGTGTTGTTTGACAATTGGT
CATTAACTCGCTTTTATATT
TTCTTTTCTCTTAGGAAAGG
TGATCCTGATAATTTATATT
GGAACACTTTTTTTTTCTCT
CACTAGCTTT

SEQ ID NO: 12:
Coding sequence
of the alpha-
WOLF 27 allele

ATGGCCGAAATCGGATACTC
GGTTTGTGCGAAACTCATCG
AAGTGATTGGCAGTGAGCTG
ATCAAAGAGATTTGCGACAC
ATGGGGTTACAAATCTCTTC
TTGAGGACCTCAACAAAACT
GTATTGACGGTCAGGAACGT
TCTCATTCAGGCCGGGGTGA
TGCGGGAGCTTACTAGTGAA
CAACAAGGTTTCATTGCAGA
CCTTAAAGATGTTGTTTATG
ATGCTGATGACTTGTTCGAC
AAGTTACTCACTCGTGCTGA
GCGAAAACAGATTGATGGAA
ACGAAATCTCTGAAAAGGTA
CGTCGTTTCTTTTCCTCTAG
TAACAAGATCGGTCAAGCTT
ACTACATGTCTCGTAAGGTT
AAGGAAATTAAGAAGCAGTT
GGATGAAATTGTTGATAGGC
ATACAAAATTTGGGTTTAGT
GCTGAGTTTATACCTGTTTG
TAGGGAAAGGGGGAACGAGA
GGGAAACACGTTCATATATA
GATGTCAAGAATATTCTTGG
GAGGGATAAAGATAAGAATG
ATATCATAGATAGGTTGCTT
AATCGTAATGATAATGAAGC
TTGTAGTTTCCTGACCATAG
TGGGAGCGGGAGGATTGGGA
AAAACTGCTCTTGCCCAACT
TGTGTTCAATGATGAAAGGG
TCAAAATTGAGTTTCATGAT
TTGAGGTATTGGGTTTGTGT
CTCTGATCAAGATGGGGGCC
AATTTGATGTGAAAGAAATC
CTTTGTAAGATTTTAGAGGT
GGTTACTAAGGAGAAAGTTG
ATAATAGTTCCGCATTGGAA
TTGGTACAAAGCCAATTTCA
AGAGAAGTTAAGAGGAAAGA
AGTACTTCCTTGTTCTTGAT
GATGTATGGAACGAGGATCG
TGAGAAGTGGTTTAAATTGG
AAGAGTTGTTAATGTTGGGT
CAAGGGGGAAGCAAGGTTGT
AGTGACCGCACGTTCAGAGA
AGACAGCAAATGTCATAGGG
AAAAGACATTTTATACACTG
GAATGTTTGTCGCCAGATTA
TTCATGGAGCTTATTTGAAA
TGTCGGCTTTTCAGAAAGGG
CATGAGCAGGAAAACCATGA
CGAACTAGTTGATATTGGGA
AAAAGATTGTTGAAAAATGT
TATAACAATCCACTTGCTAT
AACGGTGGTAGGAAGTCTTC
TTTATGGAGAGGAGATAAGT
AAGTGGCGGTCATTTGAAAT
GAGTGAGTTGGCCAAAATTG
GCAATGGGGATAATAAGATT
TTGTCGATATTGAAGCTCAG
TTACTACAATCTTGCAAACT
CTTTGAAGAGTTGTTTTAGT
TATTGTGCAGTATTTCCCAA
GGATCATAAAATAGAGAAGG
AGATGTTGATTGACCTTTGG
ATAGCACAAGGATATGTTGT
GCCGTTGGATGGTGGTCAAA
GTATAGAAGATGCTGCCGAG
GAACATTTTGTAATTTTATT
ACGGAGATGTTTCTTTCAAG
ATGTAGTGAAGGATGTATAC
GGTGATGTTGATTCTGTTAA
AATCCACGACTTGATGCACG
ATGTCGCCCAAGAAGTGGGG
AGGGAGGAAATATGTGTAGT
GAATGCTAATACAAAGAACT

TABLE 2-continued

Sequence information.

TGGGTGATAAAATCCGTCAT
GTACATGGTGATGTCAATAG
ATATGCACAAAGAGTCTCTC
TGTGTAGCCATAAGATTCGT
TCGTATATTGGTGGTAATTG
TGAAAAACGTTGGGTGGATA
CACTAATAGACAACTGGATG
TGTCTTAGGATGTTGGACTT
GTCAAGGCCGGATGTTAAAA
ATTTGCCTAATTCAATAGGT
AAATTGTTGCACTTGAGGTA
TCTTAACCTGTCTTGTAATG
ATGATCTGTTGATACTCCCT
GATGCAATTACAAGACTGCA
TAATTTGCAGACACTGCTTT
TAAAAGATTGCGGAAGTTTA
AAGGAGTTGCCAAAAGATTT
TTGCAAATTGGTCAAACTGA
GACACTTGGATTTAAGGTAT
TGTTGGCGTTTGATTGGTAT
GCCATTGGGAATGGATATGC
TAACTAGTCTTAGAGTACTG
CCATACTTTGTGGTGGGTAG
GAAGAAACAAAGTGTTGATG
ATGAGCTGAAAGCCCTTAAA
GGCCTCACCGAGATAAAAGG
CTCCATTAATATCAAAATCT
GTGAAAATTATAGAATAGTT
GAAGGCATGAATGACACAGG
AGGAGCTGGGTATTTGAAGA
GCATGAAACATCTCACGGGG
GTTGATATTACATTTGATGG
TGGATGTGTTAACCCTGAAG
CTGTGTTGGAAACCCTAGAG
CCACCTTCAAATATCAAGAG
GTTATCTATAGATAATTACG
ATGGTACAACAATTCCAGTA
TGGGGAAGAGCAGAGATTAA
TTGGGCAATCTCCCTCTCAC
ATCTTGTCGACATTTGGTTT
TGTGGTTGTAGTAATTTGCA
GGAGATGCCAGTGCTGAGTA
AACTGCCTCATTTGAAATCA
CTGAATCTTTTTAAGTTTTG
TAAGTTAGAGTACATGGAGA
GTAGAAGCAGCAGCAGTAGC
AGTGACACAGAAGCAGCAAC
ACCAGAATTACCAACATTCT
TCCCTTCCCTTGAAAAACTT
ACACTTTGGTATCTGGAAAA
GTTGAAGGGTTTGGGGAACA
GGAGATCGAGTAGTTTTCCC
CGCCTCTCTGAATTGGAAAT
CTGGGAATGCCCAGATCTAA
CGTGGTTTCCTCCTTGTCCA
AGCCTTAAAACGTTGAAATT
GGAAAAAAACAATGAAGCGT
TGCAAATAATAGTAAAAATA
ACAACAACAAGAGGTAAAGA
AGAAAAAGAAGAAGACAAGA
ATGCTGGTGTTGGAAATTCA
CAAGATGATGACAATGTCAA
ATTACGGAAGGCGGAAATAG
ACAATCTGGGTTATCTCAAA
TCACTGCCCACAAATTGTCT
GACTCACCTCGACATTACAA
TAAGAGATTCCAAGGAGGGG
GAGGGTGAATGGGAAGTTGG
GGAGGCATTTCAGAAGTGTG
TATCTTCTTTGAGAAAGCTC
AGCATAATCGGAAATCACGG
AATAAATAAAGTGAAGAGAC
TGTCTGGAAGAACAGGGTTG
GAGCATTTCACTCTGTTGGA
CTCACTCAAATTTTCAAAGA
TAGAAGACCAGGAAGATGAG
GGCGAAGCAACATCATATATT
CTGGAAATCCTTTCCTCAAA

TABLE 2-continued

Sequence information.

ACCTCCGCAGTTTGGAAATT
AAAGGCTCTTGCAAAATGAC
AAGTTTGCCCATGGGGATGC
AGTACTTAACCTCCCTCCAA
ACCCTCCATCTATCATATTG
TGATGAATTGAATTCCCTTC
CAGAATGGATAAGCAGCTTA
TCATCTCTTCAATCCCTGTT
CATATACAATTGTCCAGCCC
TGAAATCACTACCAGAAGCA
ATGAAGAACCTCACCTCCCT
TCAGAGACTTGAGATACAGC
ATTGTCCAGACCTAGCTGAA
AGATGCAGAAACCCAACGG
GGAGGACTATCCCAAAATTC
AACACATCCCCAAAATTGAA
ATATGGTAG

SEQ ID NO: 13:
Amino acid
sequence of the
alpha-WOLF 27
allele

MAEIGYSVCAKLIEVIGSEL
IKEICDTWGYKSLLEDLNKT
VLTVRNVLIQAGVMRELTSE
QQGFIADLKDWYDADDLFDK
LLTRAERKQIDGNEISEKVR
RFFSSSNKIGQAYYMSRKVK
EIKKQLDEIVDRHTKFGFSA
EFIPVCRERGNERETRSYID
VKNILGRDKDKNDIIDRLLN
RNDNEACSFLTIVGAGGLGK
TALAQLVFNDERVKIEFHDL
RYWVCVSDQDGGQFDVKEIL
CKILEVVTKEKVDNSSALEL
VQSQFQEKLRGKKYFLVLDD
VWNEDREKWFKLEELLMLGQ
GGSKVVVTARSEKTANVIGK
RHFYTLECLSPDYSWSLFEM
SAFQKGHEQENHDELVDIGK
KIVEKCYNNPLAITVVGSLL
YGEEISKWRSFEMSELAKIG
NGDNKILSILKLSYYNLANS
LKSCFSYCAVPPKDHKIEKE
MLIDLWIAQGYVVPLDGGQS
IEDAAEEHFVILLRRCFFQD
VVKDVYGDVDSVKIHDLMHD
VAQEVGREEICVVNANTKNL
GDKIRHVHGDVNRYAQRVSL
CSHKIRSYIGGNCEKRWVDT
LIDNWMCLRMLDLSRPDVKN
LPNSIGKLLHLRYLNLSCND
DLLILPDAITRLHNLQTLLL
KDCGSLKELPKDFCKLVKLR
HLDLRYCWRLIGMPLGMDML
TSLRVLPYFVVGRKKQSVDD
ELKALKGLTEIKGSINIKIC
ENYRIVEGMNDTGGAGYLKS
MKHLTGVDITFDGGCVNPEA
VLETLEPPSNIKRLSIDNYD
GTTIPVWGRAEINWAISLSH
LVDIWFCGCSNLQEMPVLSK
LPHLKSLNLFKFCKLEYMES
RSSSSSSDTEAATPELPTFF
PSLEKLTLWYLEKLKGLGNR
RSSSFPRLSELEIWECPDLT
WFPPCPSLKTLKLEKNNEAL
QIIVKITTTRGKEEKEEDKN
AGVGNSQDDDNVKLRKAEID
NLGYLKSLPTNCLTHLDITI
RDSKEGEGEWEVGEAFQKCV
SSLRKLSIIGNHGINKVKRL
SGRTGLEHFTLLDSLKFSKI
EDQEDEGEDNIIFWKSFPQN
LRSLEIKGSCKMTSLPMGMQ
YLTSLQTLHLSYCDELNSLP
EWISSLSSLQSLFIYNCPAL
KSLPEAMKNLTSLQRLEIQH
CPDLAERCRKPNGEDYPKIQ
HIPKIEIW

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1

Testing for Resistance to *Peronospora farinosa* f. Sp. *spinaciae* in Spinach Plants The resistance to downy mildew infection was assayed as described by Irish et al. (2008; Phytopathol. 98: 894-900), using a differential set. Spinach plants of the invention were sown along with spinach plants from different other genotypes (see Table 3) in trays containing Scotts Redi-Earth medium, and fertilized twice a week after seedling emergence with Osmocote Peter's (13-13-13) fertilizer (Scotts). Plants were inoculated with a sporangial suspension (2.5× $10^5$/ml) of a pathogenic race of *Peronospora farinosa* f. sp. *spinaciae* at the first true leaf stage. In this manner, 4 officially recognized pathogenic race were tested.

The inoculated plants were placed in a dew chamber at 18° C. with 100% relative humidity for a 24 h period, and then moved to a growth chamber at 18° C. with a 12 h photoperiod for 6 days. After 6 days, the plants were returned to the dew chamber for 24 h to induce sporulation, and they were scored for disease reaction.

Plants for this specific test were scored as resistant, intermediately resistant, or susceptible based on symptoms of chlorosis and signs of pathogen sporulation on the cotyledons and true leaves, as described by Irish et al. (2007; Plant Dis. 91: 1392-1396). Plants exhibiting no evidence of chlorosis and sporulation were in this specific test considered as resistant. Resistant plants were re-inoculated to assess whether plants initially scored as resistant had escaped infection, or whether they were truly resistant. Plants that showed only symptoms of chlorosis, or sporulation occurring only on the tips of the cotyledons were scored as intermediately resistant. Plants showing more than these symptoms of downy mildew infection were scored as being susceptible.

Table 1 shows the resistance of a plant carrying the alpha-WOLF 27 allele to each one of these pathogenic races. Table 3 shows the differential set of spinach downy mildew races and the resistance of various spinach varieties (hybrids) to each one of these pathogenic races. A susceptible reaction is scored as "+" (indicating a successful infection by the fungus, with sporulation occurring on the entire cotyledon), and resistance is depicted as "−" (absence of sporulation on the cotyledons). A weak resistance response is indicated as "(−)", which in practice means a slightly reduced level of infection (with only symptoms of chlorosis, or sporulation only occurring on the tips of the cotyledons in the differential seedling test).

TABLE 3

| Races/plants | Viroflay | Resistoflay | Califlay | Clermont | Campania | Boeing | Lion | Lazio | Whale | Polka | Pigeon | Meerkat |
|---|---|---|---|---|---|---|---|---|---|---|---|---|
| Pfs: 1 | + | − | − | − | − | − | − | − | − | − | − | − |
| Pfs: 2 | + | − | + | − | − | − | − | − | − | − | − | − |
| Pfs: 3 | + | + | − | − | − | − | − | − | − | − | − | − |
| Pfs: 4 | + | + | + | − | − | − | − | − | (−) | + | − | − |
| Pfs: 5 | + | + | − | + | − | − | − | − | − | − | − | − |
| Pfs: 6 | + | + | + | + | + | − | − | − | (−) | + | − | − |
| Pfs: 7 | + | + | + | + | − | − | − | − | (−) | + | − | − |
| Pfs: 8 | + | + | − | + | + | + | − | − | − | − | − | − |
| Pfs: 9 | + | + | − | + | + | − | − | − | − | − | − | − |
| Pfs: 10 | + | + | + | + | + | + | + | − | + | + | − | − |
| Pfs: 11 | + | + | − | + | − | − | − | + | − | − | − | − |
| Pfs: 12 | + | + | − | + | + | + | − | + | − | − | − | − |
| Pfs: 13 | + | + | + | + | (−) | − | − | + | + | (−) | − | − |
| Pfs: 14 | + | + | − | + | + | + | − | + | (−) | − | + | − |
| Pfs: 15 | + | + | + | − | − | − | − | − | + | + | − | − |
| Pfs: 16 | + | + | − | + | − | − | − | + | − | − | + | + |

Example 2

Amplification of the LRR Domain-Encoding Region

The isolated genomic DNA of a spinach plant comprising the alpha-WOLF 27 allele, of which a representative sample of seed was deposited with the NCIMB under accession number NCIMB 43668 was used in polymerase chain reactions (PCR), using forward primer ACAAGTG-GATGTGTCTTAGG (SEQ ID NO: 4) and reverse primer TTCGCCCTCATCTTCCTGG (SEQ ID NO: 5). The primer pair amplifies the LRR domain-encoding region of an alpha-WOLF gene, and has been designed for selectively amplifying part of a WOLF gene, and not of other CC-NBS-LRR protein-encoding genes.

PCR conditions for amplifying the LRR domain-encoding region of an alpha-WOLF gene using primers having SEQ ID NO: 4 and SEQ ID NO: 5 were as follows, using Platinum Taq enzyme (Thermo Fisher Scientific):
 3 minutes at 95° C. (initial denaturing step)
 40 amplification cycles, each cycle consisting of: 30 seconds denaturation at 95° C., 30 seconds annealing at 60° C., and 30 seconds extension at 72° C.
 2 minutes at 72° C. (final extension step)

The isolated genomic DNA of a spinach plant of variety Viroflay comprising the beta-WOLF 0 allele was used in polymerase chain reactions (PCR), using forward primer TCACGTGGGTTGTGTTGT (SEQ ID NO: 6) and reverse primer TTCGCCCTCATCTTCCTGG (SEQ ID NO: 5). The primer pair amplifies the LRR domain-encoding region of a beta-WOLF gene, and has been designed for selectively amplifying part of a WOLF gene, and not of other CC-NBS-LRR protein-encoding genes.

PCR conditions for amplifying the LRR domain-encoding region of a beta-WOLF gene using primers having SEQ ID NO: 5 and SEQ ID NO: 6 were as follows, using Platinum Taq enzyme (Thermo Fisher Scientific):

3 minutes at 95° C. (initial denaturing step)

40 amplification cycles, each cycle consisting of: 30 seconds denaturation at 95° C., 50 seconds annealing at 58° C. and 50 seconds extension at 72° C.

2 minutes at 72° C. (final extension step)

The PCR products were visualized on agarose gel (not shown), and DNA was purified from the PCR reaction. Subsequently the sequence of the PCR products was determined using methods well known in the art.

The DNA sequence of the LRR domain of the alpha-WOLF 27 allele amplified by primers having SEQ ID NO: 4 and SEQ ID NO: 5 is provided in Table 2 under SEQ ID NO: 9.

The DNA sequence of the LRR domain of the beta-WOLF 0 allele amplified by primers having SEQ ID NO: 5 and SEQ ID NO: 6 is provided in Table 2 under SEQ ID NO: 7.

Finally, the obtained sequences were translated into the corresponding amino acid sequence of the LRR domain having SEQ ID NO: 10 and SEQ ID NO: 8 for the alpha-WOLF 27 allele and the beta-WOLF 0, respectively (See also Table 2).

If PCR products were to be sequenced using SMRT sequencing (Pacific Biosciences), PCR primers and PCR conditions were different.

To the above-mentioned forward primers the following standard amplification sequence was added: GCAGTCGAACATGTAGCTGACTCAGGTCAC (SEQ ID NO: 15).

To the reverse primer, the following standard amplification sequence was added:

```
                                    (SEQ ID NO: 16)
    TGGATCACTTGTGCAAGCATCACATCGTAG.
```

Example 3

Introducing an Alpha-WOLF 27 Allele in a Plant not Carrying the Allele

A spinach plant comprising the alpha-WOLF 27 allele, of which a representative sample of seed was deposited with the NCIMB under accession number NCIMB 43668 was crossed with a plant of variety Viroflay carrying the beta-WOLF 0 allele to obtain a F1 generation. Subsequently, a F1 plant was selfed to obtain a F2 population.

Plants of the F2 population were assayed as described in Example 1 for resistance to *Peronospora farinosa* f. sp. *spinaciae* Pfs:14, Pfs:15 and Pfs:17.

Genomic DNA of each plant of the same F2 population was isolated and used in two different polymerase chain reactions (PCR). The first PCR reaction was done using primers for amplifying the LRR domain of an alpha-WOLF allele and the second PCR reaction was done using primers for amplifying the LRR domain of a beta-WOLF allele, both as described in Example 2.

The PCR products were visualized on agarose gel (not shown), this demonstrated that approximately 75% of the plants contained an alpha-WOLF fragment, and that the remaining approximately 25% of the plants only contained a beta-WOLF fragment. The plants only comprising the beta-WOLF fragment completely correlated with the plants that scored susceptible for Pfs:14, Pfs:15 and Pfs:17.

DNA from the PCR reaction was purified, and subsequently the sequence of the PCR products was determined. The alpha-WOLF PCR products gave a sequence that corresponded to the sequence of SEQ ID NO: 9, the genomic sequence of the LRR domain of the alpha-WOLF 27 allele. The beta-WOLF PCR products gave a sequence that corresponded to the sequence of SEQ ID NO: 7 the genomic sequence of the LRR domain of the beta-WOLF 0 allele.

The invention is further described by the following numbered paragraphs:

1. An agronomically elite spinach plant comprising an allele which confers resistance to at least one *Peronospora farinosa* f. sp. *spinaciae* race when present in a spinach plant and encodes a protein that in order of increased preference has at least 96.5%, 96.8%, 97%, 97.3%, 97.5%, 97.8%, 98%, 98.3%, 98.5%, 98.8%, 99%, 99.3%, 99.5%, 99.8%, 100% sequence identity to a protein comprising an amino acid sequence SEQ ID NO: 13; wherein said protein comprises in its amino acid sequence: a) SEQ ID NO: 1, b) SEQ ID NO: 2, and wherein the LRR domain of the protein has in order of increased preference at least 95%, 95.3%, 95.5%, 95.8%, 96%, 96.3%, 96.5%, 96.8%, 97%, 97.3%, 97.5%, 97.8%, 98%, 98.3%, 98.5%, 98.8%, 99%, 99.3%, 99.5%, 99.8%, 100% sequence identity to SEQ ID NO: 10.

2. The agronomically elite spinach plant of paragraph 1, wherein the allele when homozygously present in a spinach plant encodes a protein that confers complete resistance to at least *Peronospora farinosa* f. sp. *spinaciae* races Pfs: 7, Pfs: 8, Pfs: 9, Pfs: 11, Pfs: 12, Pfs: 13, Pfs: 14, Pfs: 15, Pfs: 17.

3. The agronomically elite spinach plant of paragraph 1, wherein the allele when homozygously present in a spinach plant encodes a protein that confers complete resistance to at least *Peronospora farinosa* f. sp. *spinaciae* races Pfs: 1, Pfs: 2, Pfs: 3, Pfs: 4, Pfs: 5, Pfs: 6, Pfs: 7, Pfs: 8, Pfs: 9, Pfs: 11, Pfs: 12, Pfs: 13, Pfs: 14, Pfs: 15, Pfs: 17.

4. An agronomically elite spinach plant comprising an allele which when homozygously present in a spinach plant encodes a protein that confers complete resistance to at least *Peronospora farinosa* f. sp. *spinaciae* races Pfs: 1, Pfs: 2, Pfs: 3, Pfs: 4, Pfs: 5, Pfs: 6, Pfs: 7, Pfs: 8, Pfs: 9, Pfs: 11, Pfs: 12, Pfs: 13, Pfs: 14, Pfs: 15, Pfs: 17, wherein the allele has a nucleotide sequence which has in order of increased preference at least 95%, 95.3%, 95.5%, 95.8%, 96%, 96.3%, 96.5%, 96.8%, 97%, 97.3%, 97.5%, 97.8%, 98%, 98.3%, 98.5%, 98.8%, 99%, 99.3%, 99.5%, 99.8%, 100% sequence identity to SEQ ID NO: 12.

5. The agronomically elite spinach plant of any of the paragraphs 1 to 4, of which a representative sample of seed capable of growing into a plant comprising said allele was deposited with the NCIMB under accession number NCIMB 43668.

6. The agronomically elite spinach plant of any of the paragraphs 1 to 5, wherein the agronomically elite spinach is a plant of a hybrid variety or a plant of an inbred line.

7. A propagation material capable of developing into the agronomically elite spinach plant of any of the paragraphs 1 to 6 and wherein the propagation material comprises a microspore, a pollen, an ovary, an ovule, an embryo, an embryo sac, an egg cell, a cutting, a root tip, a hypocotyl, a cotyledon, a stem, a leaf, a flower, an anther, a seed, a meristematic cell, a protoplast, a cell, or a tissue culture thereof.

8. A cell of the agronomically elite spinach plant of any of the paragraphs 1 to 6.

9. A method of producing an F1 hybrid spinach seed comprising crossing a first parent spinach plant with a second parent spinach plant and harvesting the resultant hybrid spinach seed, wherein said first parent spinach plant and/or said second parent spinach plant is the agronomically elite spinach plant of any of the paragraphs 1 to 6.

10. The method of paragraph 9, wherein the first and/or the second parent plant is a plant of an inbred line.

11. An F1 hybrid spinach plant grown from the seed produced by the method of paragraph 9 or 10, wherein the F1 hybrid plant carries the allele which confers resistance to at least one *Peronospora farinosa* f. sp. *spinaciae* race when present in a spinach plant and encoding a CC-NBS-LRR protein that in order of increased preference has at least 96.5%, 96.8%, 97%, 97.3%, 97.5%, 97.8%, 98%, 98.3%, 98.5%, 98.8%, 99%, 99.3%, 99.5%, 99.8%, 100% sequence identity to a protein comprising an amino acid sequence SEQ ID NO: 13; wherein said protein comprises in its amino acid sequence: (a) SEQ ID NO: 1, (b) SEQ ID NO: 2, and wherein the LRR domain of the protein has in order of increased preference at least 95%, 95.3%, 95.5%, 95.8%, 96%, 96.3%, 96.5%, 96.8%, 97%, 97.3%, 97.5%, 97.8%, 98%, 98.3%, 98.5%, 98.8%, 99%, 99.3%, 99.5%, 99.8%, 100% sequence identity to SEQ ID NO: 10.

12. A method for producing a spinach plant showing resistance to *Peronospora farinosa* f. sp. *spinaciae* comprising: (a) crossing the agronomically elite spinach plant of any of the paragraphs 1 to 6 with another spinach plant; (b) optionally performing one or more rounds of selfing and/or crossing; (c) optionally selecting after the crossing or the one or more rounds of selfing and/or crossing for a plant that comprises said allele.

13. The method of paragraph 12, wherein the method includes performing the optional selection, and the selection of the plant comprising the allele expressing the protein comprises determining the presence of the allele according to a method comprising any or more of; determining the presence of a genomic nucleotide sequence in the genome of a plant, wherein said sequence in order of increased preference at least 90%, 90.5%, 91%, 91.5%, 92%, 92.5%, 93%, 93.5%, 94%, 95%, 95.5%, 96%, 96.5%, 97%, 97.5%, 98%, 98.5%, 99%, 99.5%, 100% sequence identity to SEQ ID NO: 11, or determining the presence of a nucleotide sequence in a plant, wherein said sequence has in order of increased preference at least 97.8%, 98%, 98.3%, 98.5%, 98.8%, 99%, 99.3%, 99.5%, 99.8%, 100% sequence identity to SEQ ID NO: 12, or determining the presence of a LRR domain as having in order of increased preference at least 97%, 97.3%, 97.5%, 97.8%, 98%, 98.3%, 98.5%, 98.8%, 99%, 99.3%, 99.5%, 99.8%, 100% sequence identity to SEQ ID NO: 9.

14. The method of paragraph 12 or 13, wherein the method includes performing the optional one or more rounds of selfing and/or crossing and the optional selection, and the selection of the plant comprising the allele expressing the protein comprises determining the presence of the allele according to a method comprising any or more of: determining the presence of a genomic nucleotide sequence in the genome of a plant, wherein said sequence in order of increased preference at least 90%, 90.5%, 91%, 91.5%, 92%, 92.5%, 93%, 93.5%, 94%, 95%, 95.5%, 96%, 96.5%, 97%, 97.5%, 98%, 98.5%, 99%, 99.5%, 100% sequence identity to SEQ ID NO: 11, or determining the presence of a nucleotide sequence in a plant, wherein said sequence has in order of increased preference at least 97.8%, 98%, 98.3%, 98.5%, 98.8%, 99%, 99.3%, 99.5%, 99.8%, 100% sequence identity to SEQ ID NO: 12, or determining the presence of a LRR domain as having in order of increased preference at least 97%, 97.3%, 97.5%, 97.8%, 98%, 98.3%, 98.5%, 98.8%, 99%, 99.3%, 99.5%, 99.8%, 100% sequence identity to SEQ ID NO: 9.

15. A method of producing an F1 hybrid spinach seed comprising crossing a first parent spinach plant with a second parent spinach plant and harvesting the resultant hybrid spinach seed, wherein said first parent spinach plant and/or said second parent spinach plant is the agronomically elite spinach plant of any of the paragraphs 1 to 6.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

The invention claimed is:

1. A *Spinacia oleracea* plant comprising an allele designated alpha-WOLF 27,
   wherein the allele when homozygously present confers complete resistance to at least *Peronospora farinosa* f sp. *spinaciae* race Pfs: 7, Pfs: 8, Pfs: 9, Pfs: 11, Pfs: 12, Pfs: 13, Pfs: 14, Pfs: 15, and Pfs: 17,
   wherein the protein encoded by said allele is a CC-NBS-LRR protein that comprises in its amino acid sequence: a) the motif "MAEIGYSVC" (SEQ ID NO: 1) at its N-terminus; and b) the motif "KWMCLR" (SEQ ID NO: 2), and
   wherein the LRR domain of the protein has at least 97.5% sequence identity to SEQ ID NO: 10 and the DNA sequence of the LRR domain has at least 97% sequence identity to SEQ ID NO: 9, and
   wherein a representative sample of seed capable of growing into the plant comprising said allele was deposited with the NCIMB under accession number NCIMB 43668.

2. The *Spinacia oleracea* plant of claim 1, wherein the plant is an agronomically elite plant.

3. The *Spinacia oleracea* plant of claim 2, wherein the agronomically elite plant is a hybrid variety or an inbred line.

4. The *Spinacia oleracea* plant of claim 3, further comprising a genetic determinant resulting in resistance against *Peronospora farinosa* f. sp. *spinaciae* races Pfs:1 to Pfs:17.

5. A propagation material capable of developing into the *Spinacia oleracea* plant of claim 1,
   wherein the propagation material is selected from a group consisting of a microspore, a pollen, an ovary, an ovule, an embryo, an embryo sac, an egg cell, a cutting, a root, a root tip, a hypocotyl, a cotyledon, a stem, a leaf, a flower, an anther, a seed, a meristematic cell, a protoplast, a cell, or a tissue culture thereof.

6. A cell of the *Spinacia oleracea* plant of claim 1.

7. A method of producing a hybrid spinach seed, the method comprising:
   crossing the *Spinacia oleracea* plant of claim 1 with a second parent spinach plant and
   harvesting the resultant hybrid spinach seed.

8. The method of claim 7, wherein the *Spinacia oleracea* plant of claim 1 and/or the second parent spinach plant is a plant of an inbred line.

9. A hybrid spinach plant grown from the seed produced by the method of claim 7.

10. A method for identifying a spinach plant carrying an allele that when homozygously present in a spinach plant confers complete resistance to at least *Peronospora farinosa* f. sp. *spinaciae* race Pfs: 7, Pfs: 8, Pfs: 9, Pfs: 11, Pfs: 12, Pfs: 13, Pfs: 14, Pfs: 15, and Pfs: 17, wherein the protein encoded by said allele is a CC-NBS-LRR protein that comprises in its amino acid sequence: a) the motif "MAEIGYSVC" (SEQ ID NO: 1) at its N-terminus; and b) the motif "KWMCLR" (SEQ ID NO: 2); and wherein the LRR domain of the protein has at least 95% sequence identity to SEQ ID NO: 10, the method comprising:
    determining the presence of the LRR domain by determining the nucleotide sequence encoding the LRR domain or a part thereof in the spinach plant,
    wherein said nucleotide sequence has at least 97% sequence identity to SEQ ID NO: 9.

11. The method of claim 10,
    wherein the presence of the LRR domain is determined with a primer pair to amplify the nucleotide sequence encoding the LRR domain,
    wherein the forward primer has the sequence of SEQ ID NO: 4.

12. The method of claim 10,
    wherein the presence of the LRR domain is determined with a primer pair to amplify the nucleotide sequence encoding the LRR domain,
    wherein the reverse primer has the sequence of SEQ ID NO: 5.

13. A method for producing a spinach plant showing resistance to *Peronospora farinosa* f. sp. *spinaciae* the method comprising:
    (a) crossing the *Spinacia oleracea* plant of claim 1, with another plant and
    (b) selecting after step (a) or after one or more rounds of further crossing for a plant that comprises the allele that when homozygously present confers complete resistance to at least *Peronospora farinosa* f. sp. *spinaciae* race Pfs: 7, Pfs: 8, Pfs: 9, Pfs: 11, Pfs: 12, Pfs: 13, Pfs:

14, Pfs: 15, and Pfs: 17, wherein the protein encoded by said allele is a CC-NBS-LRR protein that comprises in its amino acid sequence: a) the motif "MAEIGYSVC" SEQ ID NO: 1) at its N-terminus; and b) the motif "KWMCLR" (SEQ ID NO: 2); and wherein the LRR domain of the protein has at least 95% sequence identity to SEQ ID NO: 10.

14. The method of claim 13, wherein the selection of a plant comprising the allele comprises determining the presence of the allele according a method for identifying a spinach plant carrying the allele comprising:
  determining the presence of the LRR domain by
  determining the nucleotide sequence encoding the LRR domain or a part thereof in the spinach plant,
  wherein said nucleotide sequence has at least 97% sequence identity to SEQ ID NO: 9.

15. The method of claim 13, further comprising a step (a') between (a) and (b) and comprising selfing in step (b), wherein step (a') and step (b) comprise:
  (a') performing one or more rounds of selfing and/or crossing and
  (b) selecting after one or more rounds of selfing and/or crossing for a plant that comprises the allele.

16. The method of claim 10, wherein the LRR domain of the protein has at least 97.5% sequence identity to SEQ ID NO: 10.

17. The *Spinacia oleracea* of claim 1, wherein the LRR domain of the protein has at least 98% sequence identity to SEQ ID NO: 10.

18. The *Spinacia oleracea* of claim 1, wherein the LRR domain of the protein has at least 98.5% sequence identity to SEQ ID NO: 10.

19. The *Spinacia oleracea* of claim 1, wherein the LRR domain of the protein has at least 99% sequence identity to SEQ ID NO: 10.

20. The *Spinacia oleracea* of claim 1, wherein the LRR domain of the protein has at least 99.5% sequence identity to SEQ ID NO: 10.

21. The *Spinacia oleracea* of claim 1, wherein the LRR domain of the protein has 100% sequence identity to SEQ ID NO: 10.

22. The method of claim 13, wherein the LRR domain of the protein has at least 97.5% sequence identity to SEQ ID NO: 10.

23. The method of claim 14, wherein the LRR domain of the protein has at least 97.5% sequence identity to SEQ ID NO: 10.

24. The *Spinacia oleracea* of claim 1, wherein the allele when homozygously present in a spinach plant confers complete resistance to at least *Peronospora farinosa* f. sp. *spinaciae* race Pfs: 1, Pfs: 2, Pfs: 3, Pfs: 4, Pfs: 5, Pfs: 6, Pfs: 7, Pfs: 8, Pfs: 9, Pfs: 11, Pfs: 12, Pfs: 13, Pfs: 14, Pfs: 15, Pfs: 17.

* * * * *

SEQUENCE LISTING

```
<160> NUMBER OF SEQ ID NOS: 16

<210> SEQ ID NO 1
<211> LENGTH: 9
<212> TYPE: PRT
<213> ORGANISM: Spinacia oleracea
<220> FEATURE:
<223> OTHER INFORMATION: motif

<400> SEQUENCE: 1

Met Ala Glu Ile Gly Tyr Ser Val Cys
1               5

<210> SEQ ID NO 2
<211> LENGTH: 6
<212> TYPE: PRT
<213> ORGANISM: Spinacia oleracea
<220> FEATURE:
<223> OTHER INFORMATION: motif

<400> SEQUENCE: 2

Lys Trp Met Cys Leu Arg
```

<210> SEQ ID NO 3
<211> LENGTH: 8
<212> TYPE: PRT
<213> ORGANISM: Spinacia oleracea
<220> FEATURE:
<223> OTHER INFORMATION: motif

<400> SEQUENCE: 3

His Val Gly Cys Val Val Asp Arg
1               5

<210> SEQ ID NO 4
<211> LENGTH: 20
<212> TYPE: DNA
<213> ORGANISM: Spinacia oleracea
<220> FEATURE:
<223> OTHER INFORMATION: Forward primer LRR domain (Alpha)

<400> SEQUENCE: 4
acaagtggat gtgtcttagg                                           20

<210> SEQ ID NO 5
<211> LENGTH: 19
<212> TYPE: DNA
<213> ORGANISM: Spinacia oleracea
<220> FEATURE:
<223> OTHER INFORMATION: Reverse primer LRR domain (Alpha)

<400> SEQUENCE: 5
ttcgccctca tcttcctgg                                            19

<210> SEQ ID NO 6
<211> LENGTH: 18
<212> TYPE: DNA
<213> ORGANISM: Spinacia oleracea
<220> FEATURE:
<223> OTHER INFORMATION: Forward primer LRR domain (Beta)

<400> SEQUENCE: 6
tcacgtgggt tgtgttgt                                             18

<210> SEQ ID NO 7
<211> LENGTH: 1597
<212> TYPE: DNA
<213> ORGANISM: Spinacia oleracea
<220> FEATURE:
<223> OTHER INFORMATION: Amplicon of LRR domain of the beta-WOLF 0
      allele (Viroflay)

<400> SEQUENCE: 7
tcacgtgggt tgtgttgtcg atagagatcc agaaatagtc tttttatgta gcaataagat    60
tcgttcgtat attagcggtc gctgcataaa gaatccggtg gattcacaaa tagcaactg    120 gatgtgcctt agggtgttgg acttgtcaga ttcatgtgtt aaagatttgt ctgattcaat   180
aggtaagctg ctgcacttaa ggtatcttaa cctctcttct aatataaagt tggagataat   240
ccctgatgca attacaagac tgcataactt gcagacacta cttttagaag attgcagaag   300
tttaaaggag ttgccaaaag attttttgcaa attggtcaaa ctgaggcact tggaattaca   360
gggttgtcat gatttgattg gtatgtcatt tggaatggat aagctaacta gtcttagaat   420
actaccaaac attgtggtgg gtaggaagga acaaagtgtt gatgatgagc tgaaagccct   480
aaaaggcctc accgagataa aaggctccat tgatatcaca atctattcaa aatatagaag   540

```
agttgaaggc atgaatggca caggaggagg agctgggtat ttgaagagca tgaaacatct    600
cacgggggtt aatattacat ttgatgaagg tggatgtgtt aaccctgaag ctgtgtattt    660
gaagagcatg aaacatctca cgagggttat tattatattt gattataaag gtggatgtgt    720
taaccctgaa gctgtgttgg caaccctaga gccaccttca aatatcaaga ggttagagat    780
gtggcattac agtggtacaa caattccagt atggggaaga gcagagatta ttgggcaat    840 ctccctctca catcttgtcg acatcacgct gaagattgt tacaatttgc aggagatgcc    900
agtgctgagt aaactgcctc atttgaaatc actggaactt acagagttgg ataacttaga    960
gtacatggag agtagaagca gcagcagtag cagtgacaca gaagcagcaa caccagaatt   1020
accaacattc ttcccttccc ttgaaaaact tacactttgg cgtctggaca gttgaaggg    1080 ttttgggaac aggagatcga gtagttttcc ccgcctctct aaattggaaa tctgaaaatg   1140
tccagatcta acgtcatttc cttcttgtcc aagccttgaa gagttggaat tgaaagaaaa   1200
caatgaagcg ttgcaaataa tagtaaaaat aacaacaaca agaggtaaag aagaaaaaga   1260
agaagacaag aatgctggtg ttggaaattc acaagatgat gacaatgtca aattatggaa   1320
ggtggaaata gacaatctgg gttatctcaa atcactgccc acaaattgtc tgactcacct   1380
cgaccttaca ataagtgatt ccaaggaggg ggagggtgaa tgggaagttg gggatgcatt   1440
tcagaagtgt gtatcttctt tgagaagcct caccataatc ggaaatcacg gaataaataa   1500
agtgaagaga ctgtctggaa gaacagggtt ggagcatttc actctgttgg aatcactcaa   1560
actttcagat atagaagacc aggaagatga gggcgaa                            1597

<210> SEQ ID NO 8
<211> LENGTH: 532
<212> TYPE: PRT
<213> ORGANISM: Spinacia oleracea
<220> FEATURE:
<223> OTHER INFORMATION: Amino acid sequence encoded by amplicon of LRR
      domain Beta Wolf 0 (Viroflay)

<400> SEQUENCE: 8

His Val Gly Cys Val Val Asp Arg Asp Pro Glu Ile Val Phe Leu Cys
1               5                   10                  15

Ser Asn Lys Ile Arg Ser Tyr Ile Ser Gly Arg Cys Ile Lys Asn Pro
            20                  25                  30

Val Asp Ser Gln Ile Asp Asn Trp Met Cys Leu Arg Val Leu Asp Leu
        35                  40                  45

Ser Asp Ser Cys Val Lys Asp Leu Ser Asp Ser Ile Gly Lys Leu Leu
    50                  55                  60

His Leu Arg Tyr Leu Asn Leu Ser Ser Asn Ile Lys Leu Glu Ile Ile
65                  70                  75                  80

Pro Asp Ala Ile Thr Arg Leu His Asn Leu Gln Thr Leu Leu Leu Glu
                85                  90                  95

Asp Cys Arg Ser Leu Lys Glu Leu Pro Lys Asp Phe Cys Lys Leu Val
            100                 105                 110

Lys Leu Arg His Leu Glu Leu Gln Gly Cys His Asp Leu Ile Gly Met
        115                 120                 125

Ser Phe Gly Met Asp Lys Leu Thr Ser Leu Arg Ile Leu Pro Asn Ile
    130                 135                 140

Val Val Gly Arg Lys Glu Gln Ser Val Asp Asp Glu Leu Lys Ala Leu
145                 150                 155                 160

Lys Gly Leu Thr Glu Ile Lys Gly Ser Ile Asp Ile Thr Ile Tyr Ser
```

```
                165                 170                 175
Lys Tyr Arg Arg Val Glu Gly Met Asn Gly Thr Gly Gly Ala Gly
            180                 185                 190

Tyr Leu Lys Ser Met Lys His Leu Thr Gly Val Asn Ile Thr Phe Asp
            195                 200                 205

Glu Gly Gly Cys Val Asn Pro Glu Ala Val Tyr Leu Lys Ser Met Lys
            210                 215                 220

His Leu Thr Arg Val Ile Ile Ile Phe Asp Tyr Lys Gly Gly Cys Val
225                 230                 235                 240

Asn Pro Glu Ala Val Leu Ala Thr Leu Glu Pro Pro Ser Asn Ile Lys
                245                 250                 255

Arg Leu Glu Met Trp His Tyr Ser Gly Thr Thr Ile Pro Val Trp Gly
                260                 265                 270

Arg Ala Glu Ile Asn Trp Ala Ile Ser Leu Ser His Leu Val Asp Ile
                275                 280                 285

Thr Leu Glu Asp Cys Tyr Asn Leu Gln Glu Met Pro Val Leu Ser Lys
                290                 295                 300

Leu Pro His Leu Lys Ser Leu Glu Leu Thr Glu Leu Asp Asn Leu Glu
305                 310                 315                 320

Tyr Met Glu Ser Arg Ser Ser Ser Ser Ser Asp Thr Glu Ala Ala
                325                 330                 335

Thr Pro Glu Leu Pro Thr Phe Phe Pro Ser Leu Glu Lys Leu Thr Leu
                340                 345                 350

Trp Arg Leu Asp Lys Leu Lys Gly Phe Gly Asn Arg Arg Ser Ser Ser
                355                 360                 365

Phe Pro Arg Leu Ser Lys Leu Glu Ile Trp Lys Cys Pro Asp Leu Thr
                370                 375                 380

Ser Phe Pro Ser Cys Pro Ser Leu Glu Glu Leu Glu Leu Lys Glu Asn
385                 390                 395                 400

Asn Glu Ala Leu Gln Ile Ile Val Lys Ile Thr Thr Thr Arg Gly Lys
                405                 410                 415

Glu Glu Lys Glu Glu Asp Lys Asn Ala Gly Val Gly Asn Ser Gln Asp
                420                 425                 430

Asp Asp Asn Val Lys Leu Trp Lys Val Glu Ile Asp Asn Leu Gly Tyr
                435                 440                 445

Leu Lys Ser Leu Pro Thr Asn Cys Leu Thr His Leu Asp Leu Thr Ile
                450                 455                 460

Ser Asp Ser Lys Glu Gly Glu Gly Glu Trp Glu Val Gly Asp Ala Phe
465                 470                 475                 480

Gln Lys Cys Val Ser Ser Leu Arg Ser Leu Thr Ile Ile Gly Asn His
                485                 490                 495

Gly Ile Asn Lys Val Lys Arg Leu Ser Gly Arg Thr Gly Leu Glu His
                500                 505                 510

Phe Thr Leu Leu Glu Ser Leu Lys Leu Ser Asp Ile Glu Asp Gln Glu
                515                 520                 525

Asp Glu Gly Glu
            530

<210> SEQ ID NO 9
<211> LENGTH: 1392
<212> TYPE: DNA
<213> ORGANISM: Spinacia oleracea
<220> FEATURE:
<223> OTHER INFORMATION: Amplicon of LRR domain of the alpha-WOLF 27
      allele
```

<400> SEQUENCE: 9

```
tggatgtgtc ttaggatgtt ggacttgtca aggccggatg ttaaaaattt gcctaattca    60
ataggtaaat tgttgcactt gaggtatctt aacctgtctt gtaatgatga tctgttgata   120
ctccctgatg caattacaag actgcataat ttgcagacac tgcttttaaa agattgcgga   180
agtttaaagg agttgccaaa agattttttgc aaattggtca aactgagaca cttggattta   240
aggtattgtt ggcgtttgat tggtatgcca ttgggaatgg atatgctaac tagtcttaga   300
gtactgccat actttgtggt gggtaggaag aaacaaagtg ttgatgatga gctgaaagcc   360
cttaaaggcc tcaccgagat aaaaggctcc attaatatca aaatctgtga aaattataga   420
atagttgaag gcatgaatga cacaggagga gctgggtatt tgaagagcat gaaacatctc   480
acggggttg atattacatt tgatggtgga tgtgttaacc ctgaagctgt gttggaaacc    540
ctagagccac cttcaaatat caagaggtta tctatagata attacgatgg tacaacaatt   600
ccagtatggg gaagagcaga gattaattgg gcaatctccc tctcacatct tgtcgacatt   660
tggttttgtg gttgtagtaa tttgcaggag atgccagtgc tgagtaaact gcctcatttg   720
aaatcactga atctttttaa gttttgtaag ttagagtaca tggagagtag aagcagcagc   780
agtagcagtg acacagaagc agcaacacca gaattaccaa cattcttccc ttcccttgaa   840
aaacttacac tttggtatct ggaaaagttg aagggtttgg ggaacaggag atcgagtagt   900
tttccccgcc tctctgaatt ggaaatctgg gaatgcccag atctaacgtg gtttcctcct   960
tgtccaagcc ttaaaacgtt gaaattggaa aaaaacaatg aagcgttgca ataatagta    1020
aaaataacaa caacaagagg taaagaagaa aagaagaag acaagaatgc tggtgttgga  1080
aattcacaag atgatgacaa tgtcaaatta cggaaggcgg aaatagacaa tctgggttat  1140
ctcaaatcac tgcccacaaa ttgtctgact cacctcgaca ttacaataag agattccaag  1200
gaggggagg gtgaatggga agttggggag gcatttcaga agtgtgtatc ttcttttgaga  1260
aagctcagca taatcggaaa tcacggaata aataaagtga agagactgtc tggaagaaca  1320
gggttggagc atttcactct gttggactca ctcaaatttt caagagataga agaccaggaa  1380
gatgagggcg aa                                                       1392
```

<210> SEQ ID NO 10
<211> LENGTH: 464
<212> TYPE: PRT
<213> ORGANISM: Spinacia oleracea
<220> FEATURE:
<223> OTHER INFORMATION: Amino acid sequence encoded by amplicon of LRR
      domain of alpha-WOLF 27

<400> SEQUENCE: 10

```
Trp Met Cys Leu Arg Met Leu Asp Leu Ser Arg Pro Asp Val Lys Asn
1               5                   10                  15

Leu Pro Asn Ser Ile Gly Lys Leu Leu His Leu Arg Tyr Leu Asn Leu
            20                  25                  30

Ser Cys Asn Asp Asp Leu Leu Ile Leu Pro Asp Ala Ile Thr Arg Leu
        35                  40                  45

His Asn Leu Gln Thr Leu Leu Lys Asp Cys Gly Ser Leu Lys Glu
    50                  55                  60

Leu Pro Lys Asp Phe Cys Lys Leu Val Lys Leu Arg His Leu Asp Leu
65                  70                  75                  80

Arg Tyr Cys Trp Arg Leu Ile Gly Met Pro Leu Gly Met Asp Met Leu
                85                  90                  95
```

```
Thr Ser Leu Arg Val Leu Pro Tyr Phe Val Gly Arg Lys Lys Gln
            100                 105                 110

Ser Val Asp Asp Glu Leu Lys Ala Leu Lys Gly Leu Thr Glu Ile Lys
        115                 120                 125

Gly Ser Ile Asn Ile Lys Ile Cys Glu Asn Tyr Arg Ile Val Glu Gly
    130                 135                 140

Met Asn Asp Thr Gly Gly Ala Gly Tyr Leu Lys Ser Met Lys His Leu
145                 150                 155                 160

Thr Gly Val Asp Ile Thr Phe Asp Gly Gly Cys Val Asn Pro Glu Ala
                165                 170                 175

Val Leu Glu Thr Leu Glu Pro Pro Ser Asn Ile Lys Arg Leu Ser Ile
            180                 185                 190

Asp Asn Tyr Asp Gly Thr Thr Ile Pro Val Trp Gly Arg Ala Glu Ile
        195                 200                 205

Asn Trp Ala Ile Ser Leu Ser His Leu Val Asp Ile Trp Phe Cys Gly
    210                 215                 220

Cys Ser Asn Leu Gln Glu Met Pro Val Leu Ser Lys Leu Pro His Leu
225                 230                 235                 240

Lys Ser Leu Asn Leu Phe Lys Phe Cys Lys Leu Glu Tyr Met Glu Ser
                245                 250                 255

Arg Ser Ser Ser Ser Ser Ser Asp Thr Glu Ala Ala Thr Pro Glu Leu
            260                 265                 270

Pro Thr Phe Phe Pro Ser Leu Glu Lys Leu Thr Leu Trp Tyr Leu Glu
        275                 280                 285

Lys Leu Lys Gly Leu Gly Asn Arg Arg Ser Ser Phe Pro Arg Leu
    290                 295                 300

Ser Glu Leu Glu Ile Trp Glu Cys Pro Asp Leu Thr Trp Phe Pro Pro
305                 310                 315                 320

Cys Pro Ser Leu Lys Thr Leu Lys Leu Glu Lys Asn Asn Glu Ala Leu
                325                 330                 335

Gln Ile Ile Val Lys Ile Thr Thr Arg Gly Lys Glu Glu Lys Glu
            340                 345                 350

Glu Asp Lys Asn Ala Gly Val Gly Asn Ser Gln Asp Asp Asn Val
        355                 360                 365

Lys Leu Arg Lys Ala Glu Ile Asp Asn Leu Gly Tyr Leu Lys Ser Leu
    370                 375                 380

Pro Thr Asn Cys Leu Thr His Leu Asp Ile Thr Ile Arg Asp Ser Lys
385                 390                 395                 400

Glu Gly Glu Gly Glu Trp Glu Val Gly Glu Ala Phe Gln Lys Cys Val
                405                 410                 415

Ser Ser Leu Arg Lys Leu Ser Ile Ile Gly Asn His Gly Ile Asn Lys
            420                 425                 430

Val Lys Arg Leu Ser Gly Arg Thr Gly Leu Glu His Phe Thr Leu Leu
        435                 440                 445

Asp Ser Leu Lys Phe Ser Lys Ile Glu Asp Gln Glu Asp Glu Gly Glu
    450                 455                 460

<210> SEQ ID NO 11
<211> LENGTH: 7978
<212> TYPE: DNA
<213> ORGANISM: Spinacia oleracea
<220> FEATURE:
<223> OTHER INFORMATION: genomic DNA sequence of the alpha-WOLF 27
      allele
```

```
<400> SEQUENCE: 11
gttctgtttt ttatggcaca gatatccctc atttgcagct ctacttctac aaacatcttt      60
cattctttcg ttttccttt gattcatgta acagttgaac cttctttcat gactgatata     120
gaatcaggca gctacttcac tacttctatg ttgatcttat tttgtaataa actttgatag     180
attgaataaa ggttgtttgc agtgacttct taagatgtga ttagaagtcc ataatcactt     240
taaggtagtt tttctttaca tgattaaggt ttttccgagg cctttctatt gcttgttgg      300 ttactgtcat gacatatggt ttttctttgc ttcttatatc atatggtcct cactcaattt     360
tttaatataa agtttctcat tggttgacta aatacgttta tagcaccta taatatttta     420 tttaatatac aattttatgt attttacctt tttcatattt tttcgtgatc taccttctca     480
tatgagctac actaatttgg tagctgttta tgcaaatctt gtaccaacgg ttggctattt     540
gctcaaattt ttttttttt tttcgagct agtcatttta tgatcattga agtttgctct      600
tatattatca tttatgtatt ttaccttttt tacattttt tcgtgatcta cctgctcata     660
tgagccacac taatttggta gctgcttata caattcttgt atcaacggtt ggctacttgt     720
tcaaatattt ttattttttt acgagtaagt cattttatga tcattgaagt tgctctaata     780
ttatcatgga cctattaacg catgaataat taactcggta ggaattagtt tcaaaataaa     840
attcccctca caaaaaaaaa aaaaaaaaaa aaaaaaaaa tcagaaaacc aaccttctcc     900
agtttactgt tgtctaaagc caaagagcat ggaattttcc agtaatcgca gaccccaat      960 tctcttctcc aatcgtccct gtcaatttca gcaattgaat caatcgttga ttttaggatt    1020
tgccgccaaa aaaatgaaaa atccatgaat tttagggttc aaatttgatc cgtaattggg    1080
aaaattttca gcaattgatc ttccaaatca ttcatacttg tttccagact gcaaatgaaa    1140
ggtgcgaact ttatactgca tttttgattt ccattactgt aatttattaa gatgaactgc    1200
aatttgcaat tgttttattc gactactcat ctttaaatca aattgctaaa ttgctagcta    1260
attttcttat catattgcca aaaatttgtt gcttaaatga ttccattct ctaattattt     1320 ttgtttattt ggtagataaa taattaaata tcagccccat taattgaata ttcaaaggaa    1380
atgtatggtc caaaatggc gtttaatagt caatgccgtg ttttatgggg tggtggagta     1440
ctatatgact gtgtgtggac ttggagaaga ctagagagta ttgattatca aaatatggac    1500
cctgaaaatg aaaatgaaaa tgatgttttt acactttaaa atcgtcaaga acaacaatc     1560 ctcttagca atagtattta cacgcgttat ttgcacggac ttcaatgcaa atagtataaa     1620
tttacagtca aagttttcat tctaaagcgt aaataacttt catgaatgga ggacggtagt    1680
ataagtataa cgttatggcc taccattttc ttatcatatt cacataaatt tgttgctaaa    1740
agttgtttta cttggctaaa atacttttgt tcttattggc agataaacat cagtccatta    1800
ttggccaact tgaacatata cctccaaaca ataatcaata atgtcgatta tgaagtttgt    1860
gaatgcaatt tattatcact ttcatttata aaatgactac ttgattaaca catacaaatt    1920 taccttttctc caaacaccct ttcaattctg cttaatcttg ttttctcatc atctcttcat    1980
ctttctgaaa acacaaccca atggccgaaa tcggatactc ggtttgtgcg aaactcatcg    2040
aagtgattgg cagtgagctg atcaaagaga tttgcgacac atggggttac aaatctcttc    2100
ttgaggacct caacaaaact gtattgacgg tcaggaacgt tctcattcag gccggggtga    2160
tgcgggagct tactagtgaa caacaaggtt tcattgcaga ccttaaagat gttgtttatg    2220
atgctgatga cttgttcgac aagttactca ctcgtgctga gcgaaaacag attgatggaa    2280
acgaaatctc tgaaaaggta cgtcgtttct tttcctctag taacaagatc ggtcaagctt    2340
```

```
actacatgtc tcgtaaggtt aaggaaatta agaagcagtt ggatgaaatt gttgataggc    2400
atacaaaatt tgggtttagt gctgagttta tacctgtttg tagggaaagg gggaacgaga    2460
gggaaacacg ttcatatata gatgtcaaga atattcttgg gagggataaa gataagaatg    2520
atatcataga taggttgctt aatcgtaatg ataatgaagc ttgtagtttc ctgaccatag    2580
tgggagcggg aggattggga aaaactgctc ttgcccaact tgtgttcaat gatgaaaggg    2640
tcaaaattga gtttcatgat ttgaggtatt gggtttgtgt ctctgatcaa gatggggcc     2700 aatttgatgt gaaagaaatc ctttgtaaga ttttagaggt ggttactaag gagaaagttg    2760
ataatagttc cgcattggaa ttggtacaaa gccaatttca agagaagtta agaggaaaga    2820
agtacttcct tgttcttgat gatgtatgga acgaggatcg tgagaagtgg tttaaattgg    2880
aagagttgtt aatgttgggt caaggggaa gcaaggttgt agtgaccgca cgttcagaga     2940
agacagcaaa tgtcataggg aaaagacatt tttatacact ggaatgtttg tcgccagatt    3000
attcatggag cttatttgaa atgtcggctt tcagaaagg gcatgagcag gaaaaccatg     3060
acgaactagt tgatattggg aaaaagattg ttgaaaaatg ttataacaat ccacttgcta    3120
taacggtggt aggaagtctt ctttatggag aggagataag taagtggcgg tcatttgaaa    3180
tgagtgagtt ggccaaaatt ggcaatgggg ataataagat tttgtcgata ttgaagctca    3240
gttactacaa tcttgcaaac tctttgaaga gttgttttag ttattgtgca gtatttccca    3300
aggatcataa aatagagaag gagatgttga ttgacctttg gatagcacaa ggatatgttg    3360
tgccgttgga tggtggtcaa agtatagaag atgctgccga ggaacatttt gtaattttat    3420
tacggagatg tttctttcaa gatgtagtga aggatgtata cggtgatgtt gattctgtta    3480
aaatccacga cttgatgcac gatgtcgccc aagaagtggg gagggaggaa atatgtgtag    3540
tgaatgctaa tacaaagaac ttgggtgata aaatccgtca tgtacatggt gatgtcaata    3600
gatatgcaca aagagtctct ctgtgtagcc ataagattcg ttcgtatatt ggtggtaatt    3660
gtgaaaaacg ttgggtggat acactaatag acaactggat gtgtcttagg atgttggact    3720
tgtcaaggcc ggatgttaaa aatttgccta attcaatagg taaattgttg cacttgaggt    3780
atcttaacct gtcttgtaat gatgatctgt tgatactccc tgatgcaatt acaagactgc    3840 ataaatttgca gacactgctt ttaaaagatt gcggaagttt aaaggagttg ccaaaagatt   3900
tttgcaaatt ggtcaaactg agacacttgg atttaaggta ttgttggcgt ttgattggta    3960
tgccattggg aatggatatg ctaactagtc ttagagtact gccatacttt gtggtgggta    4020
ggaagaaaca aagtgttgat gatgagctga agcccttaa aggcctcacc gagataaaag     4080
gctccattaa tatcaaaatc tgtgaaaatt atagaatagt tgaaggcatg aatgacacag    4140
gaggagctgg tgtatttgaag agcatgaaac atctcacggg ggttgatatt acatttgatg   4200
gtggatgtgt taaccctgaa gctgtgttgg aaaccctaga gccaccttca aatatcaaga    4260
ggttatctat agataattac gatggtacaa caattccagt atgggaaga gcagagatta     4320 attgggcaat ctccctctca catcttgtcg acatttggtt ttgtggttgt agtaatttgc    4380
aggagatgcc agtgctgagt aaactgcctc atttgaaatc actgaatctt tttaagtttt    4440
gtaagttaga gtacatggag agtagaagca gcagcagtag cagtgacaca gaagcagcaa    4500
caccagaatt accaacattc ttcccttccc ttgaaaaact tacactttgg tatctggaaa    4560
agttgaaggg tttggggaac aggagatcga gtagtttttcc ccgcctctct gaattggaaa   4620
tctgggaatg cccagatcta acgtggtttc ctccttgtcc aagccttaaa acgttgaaat    4680
```

```
tggaaaaaaa caatgaagcg ttgcaaataa tagtaaaaat aacaacaaca agaggtaaag    4740
aagaaaaaga agaagacaag aatgctggtg ttggaaattc acaagatgat gacaatgtca    4800
aattacggaa ggcggaaata gacaatctgg gttatctcaa atcactgccc acaaattgtc    4860
tgactcacct cgacattaca ataagagatt ccaaggaggg ggagggtgaa tgggaagttg    4920
gggaggcatt tcagaagtgt gtatcttctt tgagaaagct cagcataatc ggaaatcacg    4980
gaataaataa agtgaagaga ctgtctggaa gaacagggtt ggagcatttc actctgttgg    5040
actcactcaa attttcaaag atagaagacc aggaagatga gggcgaagac aacatcatat    5100
tctggaaatc ctttcctcaa aacctccgca gtttggaaat taaaggctct tgcaaaatga    5160
caagtttgcc catggggatg cagtacttaa cctccctcca aaccctccat ctatcatatt    5220
gtgatgaatt gaattccctt ccagaatgga taagcagctt atcatctctt caatccctgt    5280
tcatatacaa ttgtccagcc ctgaaatcac taccagaagc aatgaagaac ctcacctccc    5340
ttcagagact tgagatacag cattgtccag acctagctga agatgcaga aaacccaacg    5400 gggaggacta tcccaaaatt caacacatcc ccaaaattgt aagtcattgc agaaagtaat    5460
ttattcattt atatttattt tatgcttaga atgatatacg cagtcgtcct ttggtttcca    5520
atcttgaatt tggttttttgt tttctttctt tgtttctttta ttcaacacca gtccatttat    5580
gattgattca ttaaaaaaag gatggagttt tatggatttg aagaagacaa cgaattgaga    5640
ttcctggggt ttttttttttc gttggggttg gttttcatgt atatgttgct gattaaatac    5700
cagactgatg atgatgatgt gtttatgggt tttaaatcag attaaatata tgggaaatgt    5760
aagttaattg gggatgcaca taaggtgttt gatgaaatgt ctatgagaaa tgttgtttct    5820
tggacttaga atgatataca ctgtcgtcct ttggtttcca atcttacatt tggtttgtgt    5880
tttcttagtt tgtttctttta atcaacacca gcccatttt tttaaactac ctgcaactac    5940
taattttcat ttaccctgta tctcaggaaa tatggtagta attctcattt actcaacact    6000
agcttgatcc tgaacgcagc caaccttcag gttagaatcc gccttactca tccttttgtc    6060
atgcattgtt ttaagttgtt ttgcttgctt gtgtaatcat aattcatagt atacgattca    6120
tcattcacta tgtctacagg caagatattg gaattgttca cgattccctg aagtttcttt    6180 gttttttgttg ataccaccat attgcagctt atagtgacta agttaatgaa tgtttccaaa    6240
aaattagtca tataaattct tcttctctct ctattacata aactctttt ctctttctaa    6300 cttatcatgt tcatgcctaa aacttataca tgctcacatc attgttcgtt tgagctgact    6360
tacttctgta agagagctat ctagttaaca actcttgtaa cttttatttt gctagtcaga    6420
acatggattg gtgcaagcat gggaatttgc taacactcta ccaaatcgat tggagtttgg    6480
acttagtttc accagaagcc ataccccggac acttactggg gactgtcaac aaagccgcat    6540
tgtgatgtac ttggatgttt cacgtgcctg aggtgcgagt tacttggaag ggaagcggtt    6600
tatttaattg ttttcctaag tagattttgc ttacaagctt ttacttttca cttgaaaggg    6660 ttttcttgt tttaagcttt tcgaattaga gttttcggtt gcattaagag tagtcgtatt    6720
agtcttttac ctaaggaaga ctctttttg taattttcag actatgcaat tcaagttttc    6780
gagtgttttc ttgcttgtgt gattgtgagt tggtgaattc gtcttcata cattttgaga    6840 ttatcagaag ctttatgctc caccggtagt ctagtacctt ttctgttact gtacgtgcag    6900
ggaagtaatc tggtaccttc tatatatatg gaaaaacata cattatacat tatgcaaaat    6960
tcttacaggt tagttacttc ctggaacttc atttacactt tgttttttt gttccattcc    7020 ctcggaagac tattccctct gagaaatatg taatgaactt ctgtatgttg ctgtttggtt    7080
```

```
cctgttttaa tcttcaattt tcttgtatag ttacagctgc atttacaatg aagtttaagc    7140
agacactctc tttatatagt gcttctttct ggagcaccgt tgagctgtct gtggttgatc    7200
accatctgct gccgagagat tcagcaatcg cgtgtttgat caggtaaaag ttttatgtc     7260 aatgtgtttt tttttccgtt tgatcaattt atgtctgtat tcagattctt atcttcttac    7320
agtagcataa cacattgttt ctttcattta tgtaaactgt ttcaagatta cagagatgta    7380
tgcttcagtc gacattgatg ataacttaag atagcattcc tacaacagtt gcaggcgcat    7440
tctaactccg gcaattctag ttaggcaaga ggagcattgc caatacctgc cacctctggg    7500
atttactata ccagggttga agtttatgga agacaccagc tatgcacaag ccttcaaggg    7560
gtcatcctac ataacaagtt gaaccaacca attgcttgtt ggttcagtgg taattggagc    7620
tgaatttggt agggatggcc catgttcgat ccccacaaca acaattggga ggggactgga    7680
acctatccac acgaactccg ccctgaatcc ggattagtcc taagggtgaa cggggtgcta    7740
acaccaaaaa aaaaaaacat aacaagttga accaaacata ctttgtttga attgaagatt    7800
tagtgatttc atttgatcga ttgagatgtc ttattataag cgtatatgct cttggatttg    7860
gccacttagg tgttgtttga caattggtca ttaactcgct tttatatttt cttttctctt    7920
aggaaaggtg atcctgataa tttatattgg aacactttt ttttctctca ctagctttt     7978

<210> SEQ ID NO 12
<211> LENGTH: 3450
<212> TYPE: DNA
<213> ORGANISM: Spinacia oleracea
<220> FEATURE:
<223> OTHER INFORMATION: Coding sequence of the alpha-WOLF 27 allele

<400> SEQUENCE: 12
atggccgaaa tcggatactc ggtttgtgcg aaactcatcg aagtgattgg cagtgagctg      60
atcaaagaga tttgcgacac atgggggttac aaatctcttc ttgaggacct caacaaaact    120
gtattgacgg tcaggaacgt tctcattcag gccggggtga tgcgggagct tactagtgaa     180
caacaaggtt tcattgcaga ccttaaagat gttgtttatg atgctgatga cttgttcgac     240
aagttactca ctcgtgctga gcgaaaacag attgatggaa acgaaatctc tgaaaaggta     300
cgtcgtttct tttcctctag taacaagatc ggtcaagctt actacatgtc tcgtaaggtt     360
aaggaaatta gaagcagtt ggatgaaatt gttgataggc atacaaaatt tgggtttagt      420
gctgagttta tacctgtttg tagggaaagg gggaacgaga gggaaacacg ttcatatata     480
gatgtcaaga atattcttgg gagggataaa gataagaatg atatcataga taggttgctt    540
aatcgtaatg ataatgaagc ttgtagtttc ctgaccatag tgggagcggg aggattggga    600
aaaactgctc ttgcccaact tgtgttcaat gatgaaaggg tcaaaattga gtttcatgat    660
ttgaggtatt gggtttgtgt ctctgatcaa gatgggggcc aatttgatgt gaaagaaatc    720
ctttgtaaga tttagaggt ggttactaag gagaaagttg ataatagttc cgcattggaa     780
ttggtacaaa gccaatttca agagaagtta gaggaaaga agtacttcct tgttcttgat    840
gatgtatgga cgaggatcg tgagaagtgg tttaaattgg aagagttgtt aatgtttggt    900 caaggggaa gcaaggttgt agtgaccgca cgttcagaga agacagcaaa tgtcataggg    960
aaaagacatt tttatacact ggaatgtttg tcgccagatt attcatggag cttatttgaa   1020
atgtcggctt ttcagaaagg gcatgagcag gaaaaccatg acgaactagt tgatattggg   1080
aaaaagattg ttgaaaaatg ttataacaat ccacttgcta taacggtggt aggaagtctt   1140
```

```
ctttatggag aggagataag taagtggcgg tcatttgaaa tgagtgagtt ggccaaaatt      1200
ggcaatgggg ataataagat tttgtcgata ttgaagctca gttactacaa tcttgcaaac      1260
tctttgaaga gttgttttag ttattgtgca gtatttccca aggatcataa aatagagaag      1320
gagatgttga ttgacctttg gatagcacaa ggatatgttg tgccgttgga tggtggtcaa      1380
agtatagaag atgctgccga ggaacatttt gtaattttat tacggagatg tttctttcaa      1440
gatgtagtga aggatgtata cggtgatgtt gattctgtta aaatccacga cttgatgcac      1500
gatgtcgccc aagaagtggg gagggaggaa atatgtgtag tgaatgctaa tacaaagaac      1560
ttgggtgata aaatccgtca tgtacatggt gatgtcaata gatatgcaca aagagtctct      1620
ctgtgtagcc ataagattcg ttcgtatatt ggtggtaatt gtgaaaaacg ttgggtggat      1680
acactaatag acaactggat gtgtcttagg atgttggact tgtcaaggcc ggatgttaaa      1740
aatttgccta attcaatagg taaattgttg cacttgaggt atcttaacct gtcttgtaat      1800
gatgatctgt tgatactccc tgatgcaatt acaagactgc ataatttgca gacactgctt      1860
ttaaaagatt gcggaagttt aaaggagttg ccaaaagatt tttgcaaatt ggtcaaactg      1920
agacacttgg atttaaggta ttgttggcgt ttgattggta tgccattggg aatggatatg      1980
ctaactagtc ttagagtact gccatacttt gtggtgggga ggaagaaaca aagtgttgat      2040
gatgagctga aagcccttaa aggcctcacc gagataaaag gctccattaa tatcaaaatc      2100
tgtgaaaatt atagaatagt tgaaggcatg aatgacacag gaggagctgg gtatttgaag      2160
agcatgaaac atctcacggg ggttgatatt acatttgatg gtggatgtgt taaccctgaa      2220
gctgtgttgg aaaccctaga gccaccttca aatatcaaga ggttatctat agataattac      2280
gatggtacaa caattccagt atggggaaga gcagagatta attgggcaat ctccctctca      2340
catcttgtcg acatttggtt ttgtggttgt agtaatttgc aggagatgcc agtgctgagt      2400
aaactgcctc atttgaaatc actgaatctt tttaagtttt gtaagttaga gtacatggag      2460
agtagaagca gcagcagtag cagtgacaca gaagcagcaa caccagaatt accaacattc      2520
ttcccttccc ttgaaaaact tacactttgg tatctggaaa agttgaaggg tttggggaac      2580
aggagatcga gtagttttcc ccgcctctct gaattggaaa tctgggaatg cccagatcta      2640
acgtggtttc ctccttgtcc aagccttaaa acgttgaaat tggaaaaaaa caatgaagcg      2700
ttgcaaataa tagtaaaaat aacaacaaca agaggtaaag aagaaaaaga agaagacaag      2760
aatgctggtg ttggaaattc acaagatgat gacaatgtca aattacggaa ggcggaaata      2820
gacaatctgg gttatctcaa atcactgccc acaaattgtc tgactcacct cgacattaca      2880
ataagagatt ccaaggaggg ggagggtgaa tgggaagttg gggaggcatt tcagaagtgt      2940
gtatcttctt tgagaaagct cagcataatc ggaaatcacg gaataaataa agtgaagaga      3000
ctgtctggaa gaacagggtt ggagcatttc actctgttgg actcactcaa attttcaaag      3060
atagaagacc aggaagatga gggcgaagac aacatcatat tctggaaatc ctttcctcaa      3120
aacctccgca gtttggaaat taaaggctct tgcaaaatga caagtttgcc catggggatg      3180
cagtacttaa cctccctcca aaccctccat ctatcatatt gtgatgaatt gaattccctt      3240
ccagaatgga taagcagctt atcatctctt caatccctgt tcatatacaa ttgtccagcc      3300
ctgaaatcac taccagaagc aatgaagaac ctcacctccc ttcagagact tgagatacag      3360
cattgtccag acctagctga agatgcagaa aaacccaacg gggaggacta tcccaaaatt      3420
caacacatcc ccaaaattga aatatggtag                                       3450
```

-continued

<210> SEQ ID NO 13
<211> LENGTH: 1149
<212> TYPE: PRT
<213> ORGANISM: Spinacia oleracea
<220> FEATURE:
<223> OTHER INFORMATION: Amino acid sequence of the alpha-WOLF 27 allele

<400> SEQUENCE: 13

```
Met Ala Glu Ile Gly Tyr Ser Val Cys Ala Lys Leu Ile Glu Val Ile
1               5                   10                  15

Gly Ser Glu Leu Ile Lys Glu Ile Cys Asp Thr Trp Gly Tyr Lys Ser
            20                  25                  30

Leu Leu Glu Asp Leu Asn Lys Thr Val Leu Thr Val Arg Asn Val Leu
        35                  40                  45

Ile Gln Ala Gly Val Met Arg Glu Leu Thr Ser Glu Gln Gln Gly Phe
    50                  55                  60

Ile Ala Asp Leu Lys Asp Val Val Tyr Asp Ala Asp Leu Phe Asp
65                  70                  75                  80

Lys Leu Leu Thr Arg Ala Glu Arg Lys Gln Ile Asp Gly Asn Glu Ile
                85                  90                  95

Ser Glu Lys Val Arg Arg Phe Phe Ser Ser Asn Lys Ile Gly Gln
            100                 105                 110

Ala Tyr Tyr Met Ser Arg Lys Val Lys Glu Ile Lys Lys Gln Leu Asp
        115                 120                 125

Glu Ile Val Asp Arg His Thr Lys Phe Gly Phe Ser Ala Glu Phe Ile
    130                 135                 140

Pro Val Cys Arg Glu Arg Gly Asn Glu Arg Glu Thr Arg Ser Tyr Ile
145                 150                 155                 160

Asp Val Lys Asn Ile Leu Gly Arg Asp Lys Asp Lys Asn Asp Ile Ile
                165                 170                 175

Asp Arg Leu Leu Asn Arg Asn Asp Asn Glu Ala Cys Ser Phe Leu Thr
            180                 185                 190

Ile Val Gly Ala Gly Gly Leu Gly Lys Thr Ala Leu Ala Gln Leu Val
        195                 200                 205

Phe Asn Asp Glu Arg Val Lys Ile Glu Phe His Asp Leu Arg Tyr Trp
    210                 215                 220

Val Cys Val Ser Asp Gln Asp Gly Gln Phe Asp Val Lys Glu Ile
225                 230                 235                 240

Leu Cys Lys Ile Leu Glu Val Val Thr Lys Glu Lys Val Asp Asn Ser
                245                 250                 255

Ser Ala Leu Glu Leu Val Gln Ser Gln Phe Gln Glu Lys Leu Arg Gly
            260                 265                 270

Lys Lys Tyr Phe Leu Val Leu Asp Asp Val Trp Asn Glu Asp Arg Glu
        275                 280                 285

Lys Trp Phe Lys Leu Glu Glu Leu Leu Met Leu Gly Gln Gly Gly Ser
    290                 295                 300

Lys Val Val Val Thr Ala Arg Ser Glu Lys Thr Ala Asn Val Ile Gly
305                 310                 315                 320

Lys Arg His Phe Tyr Thr Leu Glu Cys Leu Ser Pro Asp Tyr Ser Trp
                325                 330                 335

Ser Leu Phe Glu Met Ser Ala Phe Gln Lys Gly His Glu Gln Glu Asn
            340                 345                 350

His Asp Glu Leu Val Asp Ile Gly Lys Lys Ile Val Glu Lys Cys Tyr
        355                 360                 365

Asn Asn Pro Leu Ala Ile Thr Val Val Gly Ser Leu Leu Tyr Gly Glu
```

```
                370             375             380
Glu Ile Ser Lys Trp Arg Ser Phe Glu Met Ser Glu Leu Ala Lys Ile
385                 390                 395                 400

Gly Asn Gly Asp Asn Lys Ile Leu Ser Ile Leu Lys Leu Ser Tyr Tyr
            405                 410                 415

Asn Leu Ala Asn Ser Leu Lys Ser Cys Phe Ser Tyr Cys Ala Val Phe
            420                 425                 430

Pro Lys Asp His Lys Ile Glu Lys Glu Met Leu Ile Asp Leu Trp Ile
            435                 440                 445

Ala Gln Gly Tyr Val Val Pro Leu Asp Gly Gln Ser Ile Glu Asp
            450                 455                 460

Ala Ala Glu Glu His Phe Val Ile Leu Leu Arg Arg Cys Phe Phe Gln
465                 470                 475                 480

Asp Val Val Lys Asp Val Tyr Gly Asp Val Ser Val Lys Ile His
            485                 490                 495

Asp Leu Met His Asp Val Ala Gln Glu Val Gly Arg Glu Glu Ile Cys
            500                 505                 510

Val Val Asn Ala Asn Thr Lys Asn Leu Gly Asp Lys Ile Arg His Val
            515                 520                 525

His Gly Asp Val Asn Arg Tyr Ala Gln Arg Val Ser Leu Cys Ser His
            530                 535                 540

Lys Ile Arg Ser Tyr Ile Gly Asn Cys Glu Lys Arg Trp Val Asp
545                 550                 555                 560

Thr Leu Ile Asp Asn Trp Met Cys Leu Arg Met Leu Asp Leu Ser Arg
            565                 570                 575

Pro Asp Val Lys Asn Leu Pro Asn Ser Ile Gly Lys Leu Leu His Leu
            580                 585                 590

Arg Tyr Leu Asn Leu Ser Cys Asn Asp Leu Leu Ile Leu Pro Asp
            595                 600                 605

Ala Ile Thr Arg Leu His Asn Leu Gln Thr Leu Leu Leu Lys Asp Cys
610                 615                 620

Gly Ser Leu Lys Glu Leu Pro Lys Asp Phe Cys Lys Leu Val Lys Leu
625                 630                 635                 640

Arg His Leu Asp Leu Arg Tyr Cys Trp Arg Leu Ile Gly Met Pro Leu
            645                 650                 655

Gly Met Asp Met Leu Thr Ser Leu Arg Val Leu Pro Tyr Phe Val Val
            660                 665                 670

Gly Arg Lys Lys Gln Ser Val Asp Asp Glu Leu Lys Ala Leu Lys Gly
            675                 680                 685

Leu Thr Glu Ile Lys Gly Ser Ile Asn Ile Lys Ile Cys Glu Asn Tyr
            690                 695                 700

Arg Ile Val Glu Gly Met Asn Asp Thr Gly Ala Gly Tyr Leu Lys
705                 710                 715                 720

Ser Met Lys His Leu Thr Gly Val Asp Ile Thr Phe Asp Gly Cys
            725                 730                 735

Val Asn Pro Glu Ala Val Leu Glu Thr Leu Glu Pro Pro Ser Asn Ile
            740                 745                 750

Lys Arg Leu Ser Ile Asp Asn Tyr Asp Gly Thr Thr Ile Pro Val Trp
            755                 760                 765

Gly Arg Ala Glu Ile Asn Trp Ala Ile Ser Leu Ser His Leu Val Asp
            770                 775                 780

Ile Trp Phe Cys Gly Cys Ser Asn Leu Gln Glu Met Pro Val Leu Ser
785                 790                 795                 800
```

-continued

```
Lys Leu Pro His Leu Lys Ser Leu Asn Leu Phe Lys Phe Cys Lys Leu
            805                 810                 815
Glu Tyr Met Glu Ser Arg Ser Ser Ser Ser Ser Asp Thr Glu Ala
        820                 825                 830
Ala Thr Pro Glu Leu Pro Thr Phe Phe Pro Ser Leu Glu Lys Leu Thr
            835                 840                 845
Leu Trp Tyr Leu Glu Lys Leu Lys Gly Leu Gly Asn Arg Arg Ser Ser
        850                 855                 860
Ser Phe Pro Arg Leu Ser Glu Leu Glu Ile Trp Glu Cys Pro Asp Leu
865                 870                 875                 880
Thr Trp Phe Pro Pro Cys Pro Ser Leu Lys Thr Leu Lys Leu Glu Lys
            885                 890                 895
Asn Asn Glu Ala Leu Gln Ile Ile Val Lys Ile Thr Thr Thr Arg Gly
        900                 905                 910
Lys Glu Glu Lys Glu Glu Asp Lys Asn Ala Gly Val Gly Asn Ser Gln
        915                 920                 925
Asp Asp Asp Asn Val Lys Leu Arg Lys Ala Glu Ile Asp Asn Leu Gly
        930                 935                 940
Tyr Leu Lys Ser Leu Pro Thr Asn Cys Leu Thr His Leu Asp Ile Thr
945                 950                 955                 960
Ile Arg Asp Ser Lys Glu Gly Glu Gly Glu Trp Glu Val Gly Glu Ala
            965                 970                 975
Phe Gln Lys Cys Val Ser Ser Leu Arg Lys Leu Ser Ile Ile Gly Asn
        980                 985                 990
His Gly Ile Asn Lys Val Lys Arg Leu Ser Gly Arg Thr Gly Leu Glu
        995                 1000                1005
His Phe Thr Leu Leu Asp Ser Leu Lys Phe Ser Lys Ile Glu Asp Gln
        1010                1015                1020
Glu Asp Glu Gly Glu Asp Asn Ile Ile Phe Trp Lys Ser Phe Pro Gln
1025                1030                1035                1040
Asn Leu Arg Ser Leu Glu Ile Lys Gly Ser Cys Lys Met Thr Ser Leu
            1045                1050                1055
Pro Met Gly Met Gln Tyr Leu Thr Ser Leu Gln Thr Leu His Leu Ser
        1060                1065                1070
Tyr Cys Asp Glu Leu Asn Ser Leu Pro Glu Trp Ile Ser Ser Leu Ser
        1075                1080                1085
Ser Leu Gln Ser Leu Phe Ile Tyr Asn Cys Pro Ala Leu Lys Ser Leu
        1090                1095                1100
Pro Glu Ala Met Lys Asn Leu Thr Ser Leu Gln Arg Leu Glu Ile Gln
1105                1110                1115                1120
His Cys Pro Asp Leu Ala Glu Arg Cys Arg Lys Pro Asn Gly Glu Asp
            1125                1130                1135
Tyr Pro Lys Ile Gln His Ile Pro Lys Ile Glu Ile Trp
            1140                1145

<210> SEQ ID NO 14
<211> LENGTH: 9
<212> TYPE: PRT
<213> ORGANISM: Spinacia oleracea
<220> FEATURE:
<223> OTHER INFORMATION: motif

<400> SEQUENCE: 14

Asp Gln Glu Asp Glu Gly Glu Asp Asn
1               5
```

```
<210> SEQ ID NO 15
<211> LENGTH: 30
<212> TYPE: DNA
<213> ORGANISM: Spinacia oleracea
<220> FEATURE:
<223> OTHER INFORMATION: standard amplification sequence forward primer

<400> SEQUENCE: 15
gcagtcgaac atgtagctga ctcaggtcac                                30

<210> SEQ ID NO 16
<211> LENGTH: 30
<212> TYPE: DNA
<213> ORGANISM: Spinacia oleracea
<220> FEATURE:
<223> OTHER INFORMATION: standard amplification sequence reverse primer

<400> SEQUENCE: 16
tggatcactt gtgcaagcat cacatcgtag                                30
```